(12) United States Patent
Handyside

(10) Patent No.: US 11,214,826 B2
(45) Date of Patent: Jan. 4, 2022

(54) CHROMOSOMAL ANALYSIS BY MOLECULAR KARYOTYPING

(75) Inventor: Alan Handyside, London (GB)

(73) Assignee: BLUEGNOME LIMITED

( * ) Notice: Subject to any disclaimer, the term of this patent is extended or adjusted under 35 U.S.C. 154(b) by 1611 days.

(21) Appl. No.: 12/093,912

(22) PCT Filed: Nov. 13, 2006

(86) PCT No.: PCT/GB2006/004221
§ 371 (c)(1),
(2), (4) Date: Aug. 25, 2008

(87) PCT Pub. No.: WO2007/057647
PCT Pub. Date: May 24, 2007

(65) Prior Publication Data
US 2008/0318235 A1    Dec. 25, 2008

(30) Foreign Application Priority Data

Nov. 15, 2005    (GB) .................................... 0523276

(51) Int. Cl.
*C12Q 1/68*    (2018.01)
*C12Q 1/6827*    (2018.01)
*C07H 21/04*    (2006.01)

(52) U.S. Cl.
CPC .................................. *C12Q 1/6827* (2013.01)

(58) Field of Classification Search
None
See application file for complete search history.

(56) References Cited

U.S. PATENT DOCUMENTS

| | | | |
|---|---|---|---|
| 5,985,538 A | 11/1999 | Stachecki | |
| 6,444,661 B1 * | 9/2002 | Barton | C07F 15/008 514/185 |
| 6,979,541 B1 | 12/2005 | Pont-Kingdom et al. | |
| 8,532,930 B2 | 9/2013 | Rabinowitz | |
| 2003/0152951 A1 * | 8/2003 | Mirel | C12Q 1/6876 435/6.13 |
| 2004/0137470 A1 * | 7/2004 | Dhallan | C12Q 1/6806 435/6.16 |
| 2004/0180362 A1 | 9/2004 | Lazar et al. | |
| 2004/0197791 A1 * | 10/2004 | Makarov | C12Q 1/6858 435/6.14 |
| 2005/0009031 A1 | 1/2005 | Becker et al. | |
| 2005/0037388 A1 | 2/2005 | Antonarakis et al. | |
| 2005/0123914 A1 * | 6/2005 | Katz et al. | 435/6 |
| 2005/0149271 A1 * | 7/2005 | Frudakis et al. | 702/20 |
| 2005/0158754 A1 * | 7/2005 | Puffenberger | C12Q 1/6879 435/6.13 |
| 2005/0191731 A1 * | 9/2005 | Judson et al. | 435/104 |
| 2005/0221332 A1 * | 10/2005 | Buchanan | C07K 14/57509 435/5 |
| 2006/0121452 A1 * | 6/2006 | Dhallan | C12Q 1/6827 435/5 |
| 2008/0085836 A1 | 4/2008 | Kearns et al. | |

FOREIGN PATENT DOCUMENTS

WO    2007062164    5/2007

OTHER PUBLICATIONS

"Chimpanzee genome project," Wikipedia.com, accessed Jun. 28, 2017.*
Handyside et al., "Pregnancies from biopsied human preimplantation embryos sexed y Y-specific DNA amplification" Nature, vol. 344, Apr. 19, 1990, pp. 768-770.*
"Oligonucleotide definition," Merriam-Webster.com (accessed Aug. 23, 2017).*
"Definition of Livestock," Merriam-Webster (accessed Nov. 26, 2017).*
"Human Hybrids," Michael F. Hammer, Scientific American, May 2013, pp. 66-71.*
"Cattle," Wikipedia.com (accessed Nov. 26, 2017).*
Handyside et al., "Pregnancies from biopsied human preimplantation embryos sexed by Y-specific DNA amplification" Nature, vol. 344, Apr. 19, 1990, pp. 768-770.*
Lareu et al., "Typing Y-chromosome single nucleotide polymorphisms with DNA microarray technology," International Congress Series, vol. 1239, 2003, pp. 21-25.*
Handyside et al., "Pregnancies from biopsied human preimplantation embryos sexed by Y-specific DNA amplification" Nature, vol. 344, Apr. 19, 1990, pp. 768-770. (Year: 1990).*
Lareu et al., "Typing Y-chromosome single nucleotide polymorphisms with DNA microarray technology," International Congress Series, vol. 1239, 2003, pp. 21-25. (Year: 2003).*
Michael F. Hammer, "Human Hybrids", Scientific American, May 2013, pp. 66-71. (Year: 2013).*
Sharon Begley, "Psst, the human genome was never completely sequenced", STATNews.com, Jun. 20, 2017. (Year: 2017).*
Affymetrix, "GeneChip human mapping 10K array and assay kit," data sheet (2003) 4 pages.
Broman, K.W. et al., "Characterization of human crossover interference," Am. J. Hum. Genet. (2000) 66:1911-1926. Bruce, S. et al., "Global analysis of uniparental disomy using high density genotyping arrays," J. Med. Genet. (2005) 42:847-851.

(Continued)

*Primary Examiner* — Bradley L. Sisson
(74) *Attorney, Agent, or Firm* — Mueting Raasch Group

(57) ABSTRACT

The invention provides a method of karyotyping (for example for the detection of trisomy) a target cell to detect chromosomal imbalance therein, the method comprising: (a) interrogating closely adjacent biallelic SNPs across the chromosome of the target cell (b) comparing the result at (a) with the SNP haplotype of paternal and maternal chromosomes to assemble a notional haplotype of target cell chromosomes of paternal origin and of maternal origin (c) assessing the notional SNP haplotype of target cell chromosomes of paternal origin and of maternal origin to detect aneuploidy of the chromosome in the target cell. Also provided are related computer-implemented embodiments and systems.

21 Claims, 16 Drawing Sheets

Figure 1A:
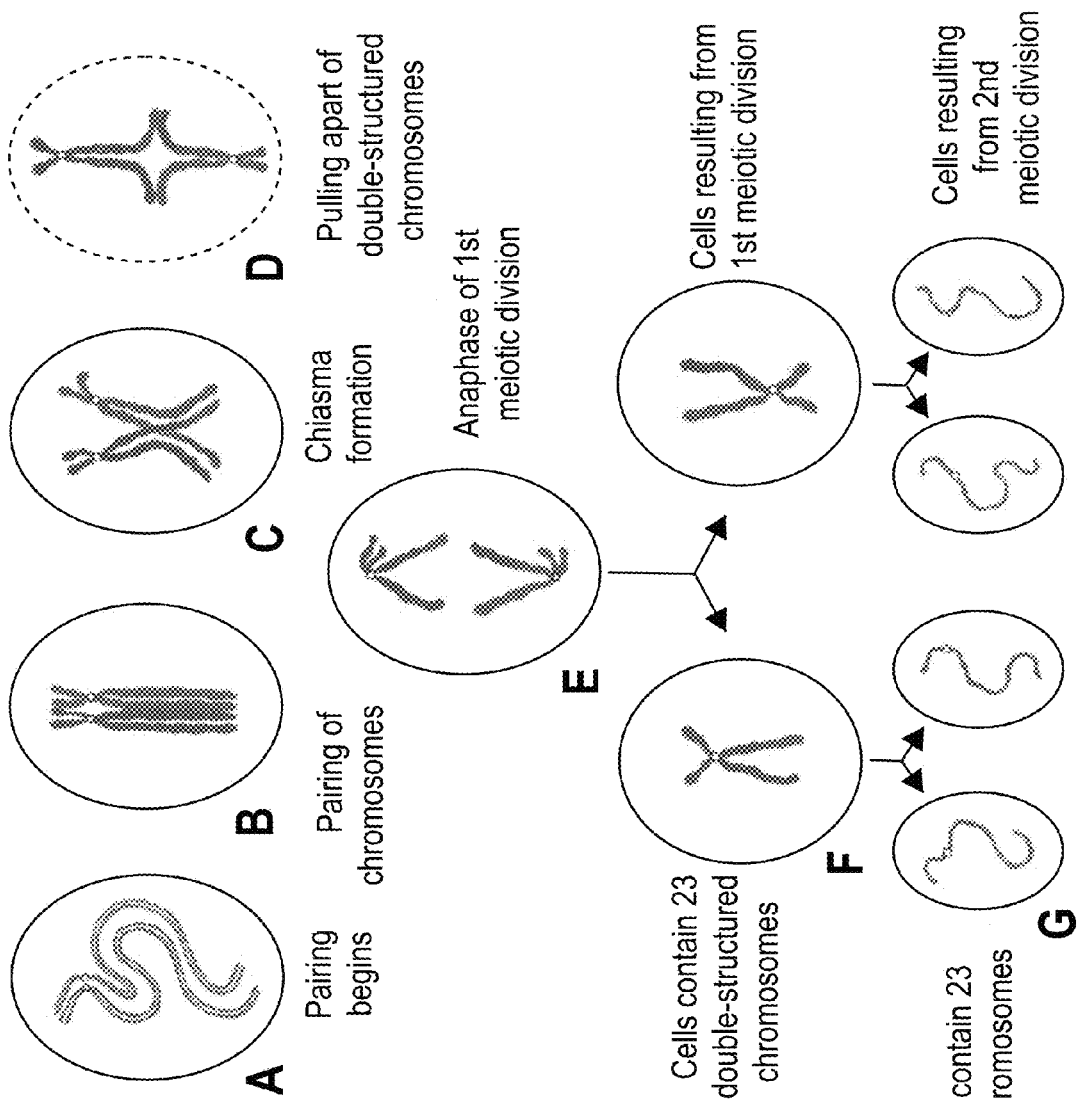

(15 of 16 Drawing Sheet(s) Filed in Color)

(56) References Cited

OTHER PUBLICATIONS

Fan, J-B. et al., "Paternal origins of complete hydatidiform moles proven by whole genome single-nucleotide polymorphism haplotyping," Genomics (2002) 79(1):58-62.

Findlay, I. et al., "Rapid trisomy diagnosis (21, 18, and 13) using fluorescent PCR and short tandem repeats applications for prenatal diagnosis and preimplantation genetic diagnosis," J. Assisted Reprod. Genetics (1998) 15 (5):266-275.

Handyside, A.H. et al., "Isothermal whole genome amplification from single and small numbers of cells: a new era for preimplantation genetic diagnosis of inhereted disease," Mol. Human Reproduction (2004) 10(10):767-772.

Heide, E. et al., "Maternal uniparental disomy (UPD) for chromosome 2 discovered by exclusion of paternity," Am. J. Med. Genet. (2000) 92:260-263.

Latour, P. et al., "Polymorphic short tandem repeats for diagnosis of the Charcot-Marie-Tooth IA duplication," Clinical Chem. (2001) 47(5):829-837.

Le Caignec, C. et al., "Detection of genomic imbalances by array based comparative genomic hybridisation in fetuses with multiple malformations," J. Med. Genet. (2005) 42:121-128.

Paperna, T. et al., "Genes for the CPE receptor (CPETR1) and the human homolog of RVP1 (CPETR2) are localized within the Williams-Beuren Syndrome deletion," Genomics (1998) 54:453-459.

Pont-Kingdom, G. et al., "Rapid detection of aneuploidy (trisomy 21) by allele quantification combined with melting curves analysis of single-nucleotide polymorphism loci," Clinical Chem. (2003) 49(7):1087-1094.

Rauch, A. et al., "Molecular karyotyping using an SNP array for genomewide genotyping," J. Med. Genet. (2004) 41:916-922.

Slater, H.R. et al., "High-resolution identification of chromosomal abnormalities using oligonucleotide arrays containing 116,204 SNPs," Am. J. Hum. Genet. (2005) 77:709-726.

Syvanen, A-C., "Toward genome-wide SNP genotyping," Nature Genetics Suppl. (2005) 37:S5-S10.

Tsui, N.B.Y. et al., "Detection of trisomy 21 by quantitative mass spectrometric analysis of single-nucleotide polymorphisms," Clin. Chem. (2005) 51(12):2358-2362.

International Search Report and Written Opinion by the International Searching Authority for PCT/GB2006/004221 dated Apr. 4, 2007 (10 pages).

International Preliminary Report on Patentability by the International Searching Authority for PCT/GB2006/004221 dated Apr. 30, 2008 (8 pages).

Written Opinion of the International Preliminary Examining Authority for PCT/GB2006/004221 dated Dec. 14, 2007 (7 pages).

Giménez et al., "Karyomapping allows preimplantation genetic diagnosis of a de-novo deletion undetectable using conventional PGD technology," 2015, Reproductive BioMedicine Online, 31:770-775.

Handyside et al., "Birth of a Normal Girl After In Vitro Fertilization and Preimplantation Diagnostic Testing for Cystic Fibrosis," Sep. 24, 1992, The New England Journal of Medicine, 327(13):905-909.

Handyside et al., "Karyomapping: a universal method for genome wide analysis of genetic disease based on mapping crossovers between parental haplotypes," Oct. 25, 2009, J. Med. Genet., 47:1-25.

Handyside et al., "Pregnancies from biopsied human preimplantation embryos sexed by Y-specific DNA amplification", Apr. 19, 1990, Nature, 344(6268):768-70.

Natesan et al., "Genome-wide karyomapping accurately identifies the inheritance of single-gene defects in human preimplantation embryos in vitro," Nov. 2014, Genetics in Medicine, 16(11): 838-845.

Wells et al., "Detailed chromosomal and molecular genetic analysis of single cells by single cells by whole genome amplification and comparative genomic hybridisation," 1999, Nucleic Acids Research, 27(4): 1214-1218.

"Gene Sheet: GeneChip Human Mapping 500K Array Set," Affymetrix, published Nov. 2, 2005, 1-4 pgs.; accessed Nov. 1, 2017 at https://tools.thermofisher.com/content/sfs/brochures/500k_datasheet.pdf.

"Single-nucleotide polymorphism," Wikipedia, the free encyclopedia, 1-11 pgs., accessed Sep. 27, 2017 at https://en.wikipedia.org/wiki/Single-nucleotide_polymorphism.

"What are single nucleotide polymorphisms (SNPs)?" Genetics Home Reference: Your Guide to Understanding Genetic Conditions, 1 pg., accessed Sep. 27, 2017 at: https://ghr.nlm.nih.gov/primer/genomicresearch/snp.

Clark et al., "Linkage disequilibrium and inference of ancestral recombination in 538 single-nucleotide polymorphism clusters across the human genome," Am. J. Hum. Genet. 2003, 73(2):285-300.

Huttley et al., "A scan for linkage disequilibrium across the human genome," Genetics 1999, 152(4): 1711-1722.

Ray et al., "Increasing the denaturation temperature during the first cycles of amplification reduces allele dropout from single cells for preimplantation genetic diagnosis," Molecular Human Reproduction, 1994;2(3):213-218.

* cited by examiner

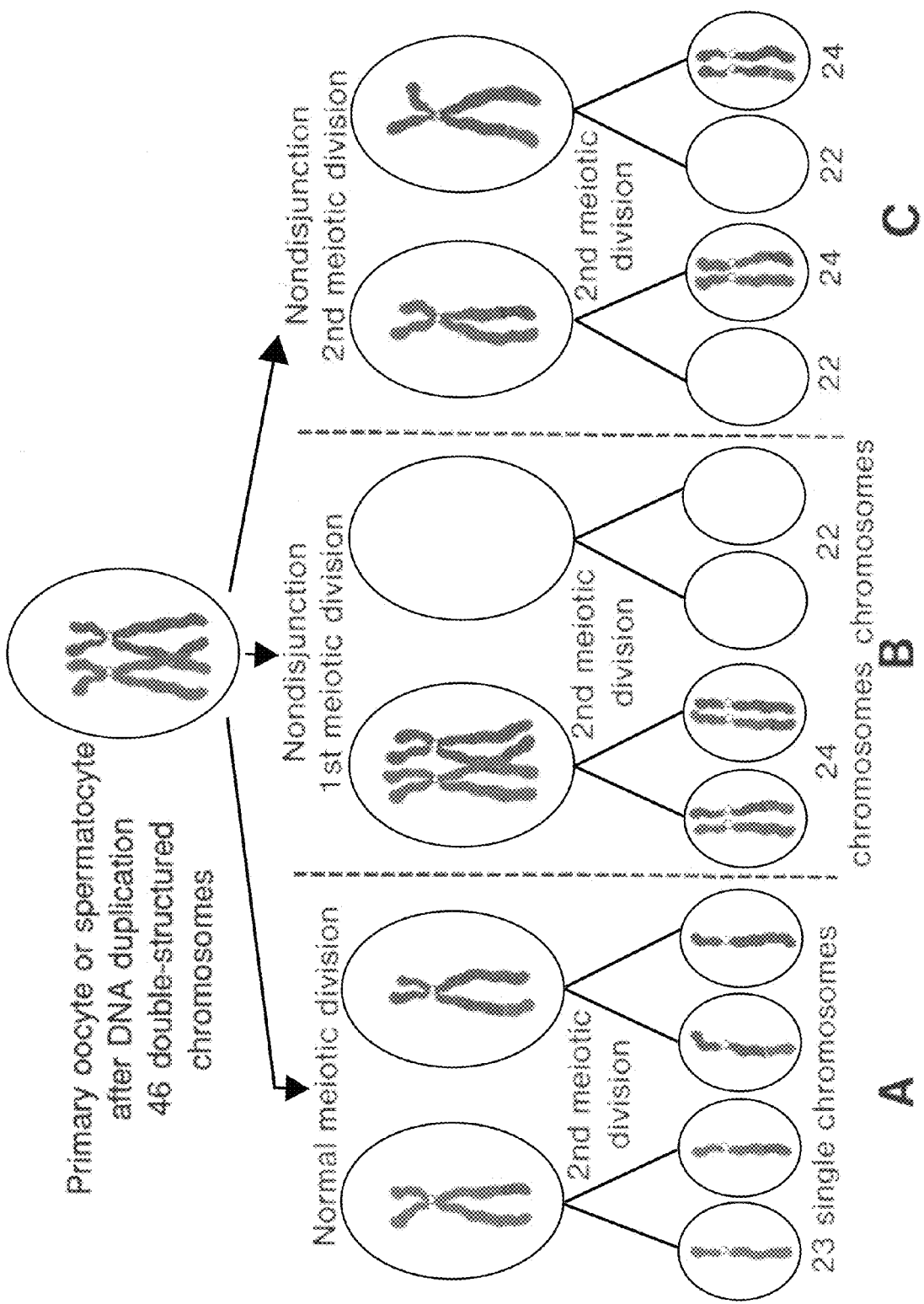

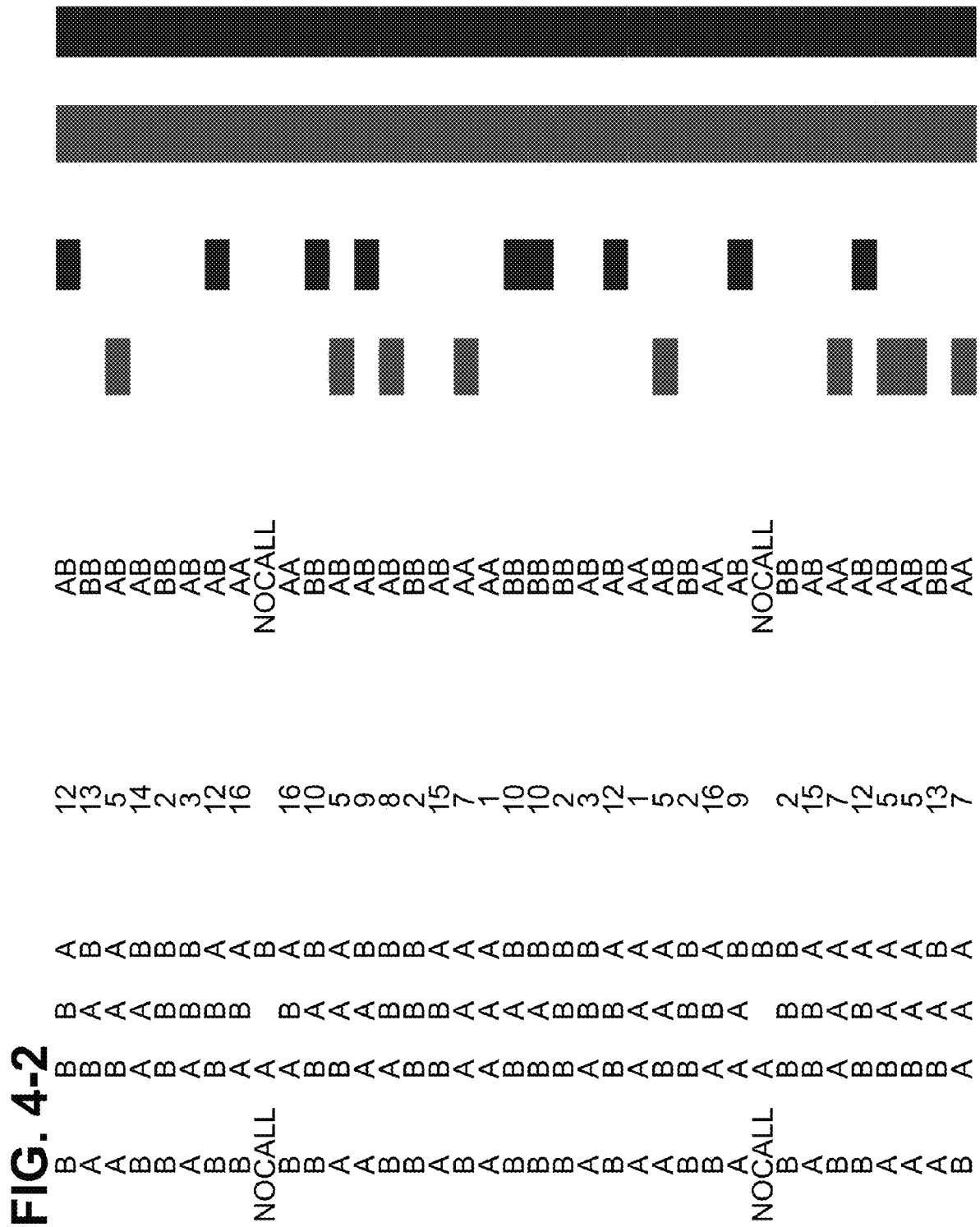

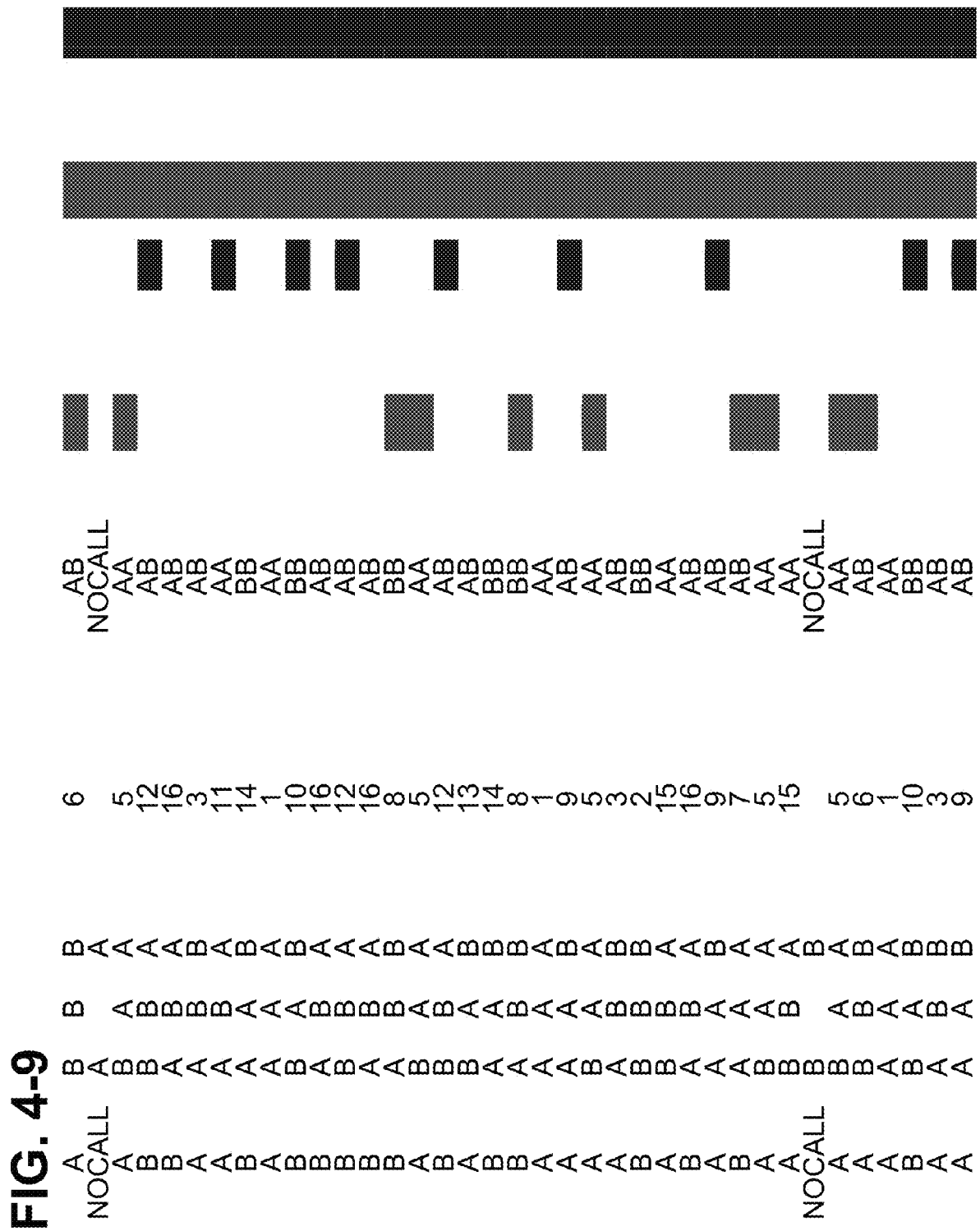

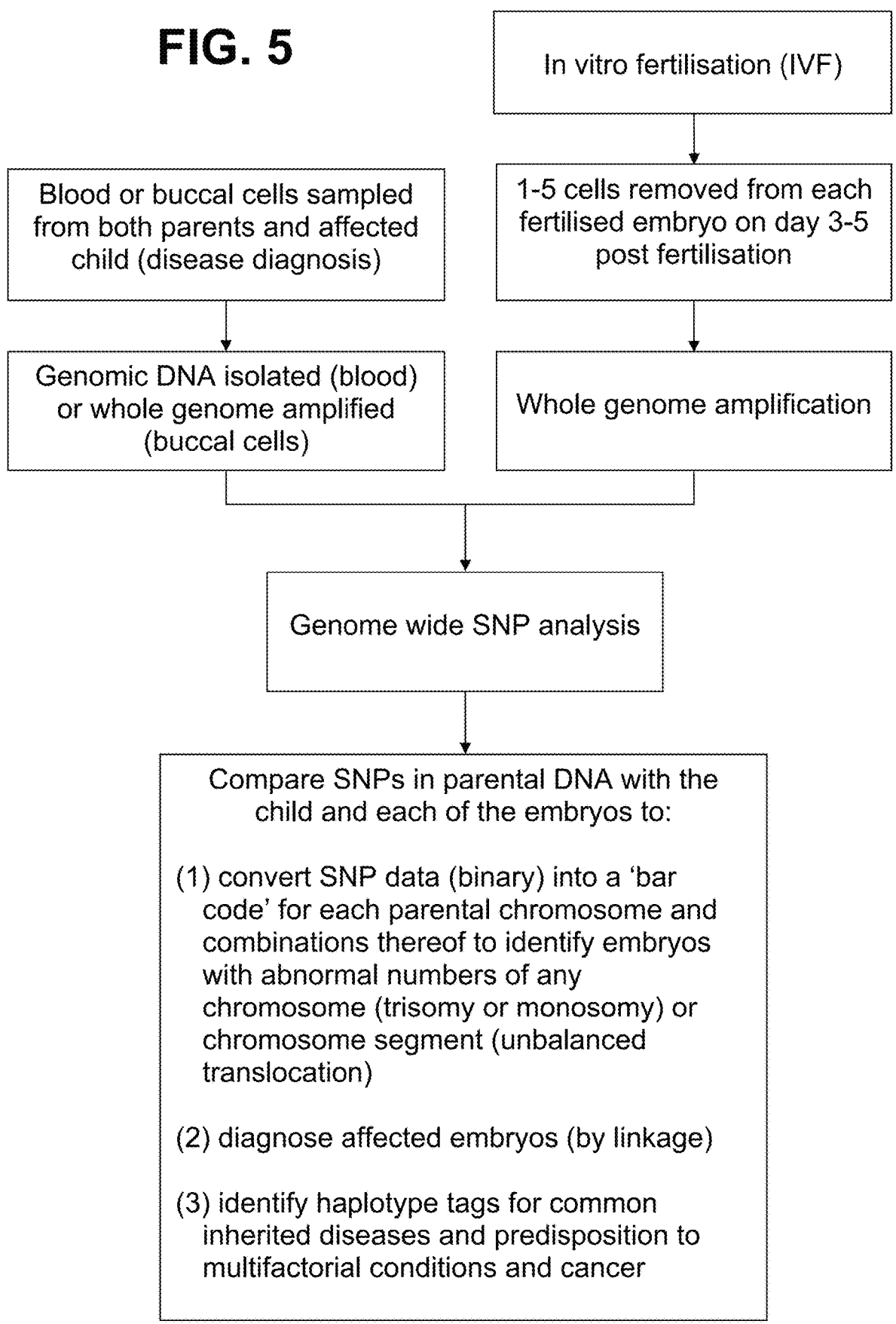

CHROMOSOMAL ANALYSIS BY MOLECULAR KARYOTYPING

CROSS-REFERENCE TO RELATED APPLICATIONS

This patent application is a national stage filing under 35 U.S.C. 371 of International Application No. PCT/GB2006/004221, filed on Nov. 13, 2006, which claims priority benefits to Great Britain Patent Application No. 0523276.4, filed Nov. 15, 2005.

TECHNICAL FIELD

The present invention relates generally to methods and materials for use in detecting abnormalities of the number of whole chromosomes or chromosome regions (aneuploidy). It has particular utility for prenatal diagnosis, either before pregnancy is established in gametes and cells taken from early embryos or later in pregnancy in samples of cells from the placenta or fetus.

BACKGROUND ART

In normal meiosis the precursor cells of the sperm or ova must multiply and then reduce the number of chromosomes to one half set in each gamete in two specialised meiotic divisions. During the early stages of meiosis following DNA replication, the four duplicated chromatids of a homologous pair align closely along their length and may exchange segments, resulting in non-recombinant (no exchange) and recombinant chromosomes and generating genetic variation. The resultant gametes, therefore, each contain a single chromosome which is either a recombinant of both homologous chromosomes or is non-recombinant and identical to one of the parental chromosomes. This is shown in FIG. 1(a).

Aneuploidy is defined as an abnormal number of whole chromosomes or parts of chromosomes causing a genetic imbalance which may be lethal at early stages of development, cause miscarriage in later pregnancy or result in a viable but abnormal pregnancy. The most frequent and clinically significant aneuploidies involve single chromosomes (strictly 'aneusomy') in which there are either three ('trisomy') or only one ('monosomy') instead of the normal pair of chromosomes.

In early development, aneuploidy can arise through abnormal chromosomal segregation following replication and cell division either (1) during the two meiotic divisions which normally result in a haploid, half set, in each gamete before fertilisation, or (2) during the early divisions of the cleavage stage fertilised embryo. FIG. 1(b) shows the effects of non-disjunction ie failure of replicated chromosomes to separate during division, which is a common cause of abnormal chromosome segregation, during the two meiotic divisions.

The aim of molecular karyotyping is to identify numerical or structural chromosomal abnormalities and in particular to identify any imbalance instead of the normal two copies of a chromosome or chromosome segment.

Currently there are two basic approaches to molecular karyotyping:

The first is to use molecular genetic markers, often highly polymorphic short tandem repeats (STRs), for each of the parental chromosomes. Where there is a different repeat on each of the parental chromosomes the STR marker is fully informative i.e. capable of identifying the presence of each chromosome (at that position). By use of a number of STR markers, the confidence in the method can be improved. An example of the use of STRs in trisomy analysis is given by Findlay et al. (1998) Journal of Assisted Reproduction and Genetics Vol 15, No 5: 1998: 266-275.

The second approach, comparative genomic hybridisation (CGH), involves fluorescent labelling of test and normal genomic DNA and comparison of quantitative differences in chromosome specific sequences by hybridising either to metaphase chromosomes or DNA clones on a microarray (array CGH). Generally test and reference DNA is labelled with different fluorochromes and hybridised to the DNA microarray with a series of cloned target DNAs, for example, BAC clones, derived from particular chromosomal regions. Such 'chips' are tailored to prenatal diagnosis and other diagnostic applications by including BACs informative, for example, for common deletion syndromes as well as aneuploidy and unbalanced translocations.

Given the importance of karyotyping, it can be seen that novel methods and materials relating to molecular karyotyping would provide a contribution to the art.

DISCLOSURE OF THE INVENTION

The present invention discloses that chromosomal analysis by molecular karyotyping, (for example for the detection of trisomy) can be performed by use of genome wide biallelic marker analysis (e.g. biallelic single nucleotide polymorphisms (SNPs)) which are distributed throughout the genome, and which can be readily detected using existing technologies.

This finding is unexpected for several reasons, principally because a priori it would be assumed that a biallelic marker (which provides only binary information at a given position on the chromosome) could not positively identify the presence of three or more different chromosomes.

Nevertheless, as described below, the invention provides that high density analysis of closely adjacent SNPs is capable of positively identifying, inter alia, the presence of two chromosomes derived from one parent and that based on well established assumptions about the frequency and spacing of recombination events between parental chromosomes during meiosis, this will allow accurate detection of trisomy.

Furthermore, the parental origin of the error is identified in each case which is not possible by some karyotyping methods.

The methods of the invention therefore do not depend on quantitation of chromosome specific sequences, as used in some currently available methods but rather compare the haplotypes of the test sample with the known haplotypes of the parents. When combined with existing methods for whole genome amplification, the methods of the invention are particularly useful where only relatively small numbers of sample cells are available for analysis.

Thus in one aspect the invention provides a method of karyotyping a target cell to detect chromosomal imbalance therein, the method comprising:

(a) interrogating closely adjacent biallelic SNPs across the chromosome of the target cell (b) comparing the result at (a) with the SNP haplotype of paternal and maternal chromosomes to assemble a notional haplotype of target cell chromosomes of paternal origin and of maternal origin (c) assessing the notional SNP haplotype of target cell chromosomes of paternal origin and of maternal origin to detect aneuploidy of the chromosome in the target cell As set out below, the method can also be used to assess chromosomal recombination, where it is desired to do so.

The target cell will be one of a sexually reproducing, diploid, species, with a genome in which biallelic SNPs occur at sufficient density to provide a notional haplotype. Preferably the cell will be an avian, reptilian, or mammalian cell. More preferably the cell is a human or non-human mammalian cell. The non-human mammal may, for instance be a primate.

In one embodiment the cell is human at least 2, 3, 4, 5, 6 or all of the human chromosomes selected from the following group are assessed: X, Y, 22, 21, 18, 16 and 13. Imbalances in any of these chromosomes may be associated with viable but abnormal pregnancies.

Preferably a total of at least 10, 15 or 20 chromosomes are assessed. In one embodiment the entire genome of the target cell (e.g. all 24 human chromosomes) is assessed.

As discussed below, SNPs can be interrogated using conventional techniques. This may be preceded by one or more conventional amplification steps. Preferably, the frequency of the less frequent allele of the biallelic markers in the present maps is at least 10, 20, or 30% (i.e. a heterozygosity rate of at least 0.18, 0.32 or 0.42).

The result of the SNP interrogation will depend on the nucleotides found at a polymorphic locus on all the copies of the given chromosome in the target cell (i.e. normally 2 copies, but may be 0, 1, or 3 where there are chromosomal abnormalities, or in the case of the X chromosome, 1 or 3 copies in a female or 0 or 2 copies in a male, and in the case of the Y chromosome, 2 copies in a male embryo). Unless context demands otherwise, where "a" or "the" chromosome is referred to herein in respect of SNP genotyping, this refers to typing all the copies of that chromosome which are present in the target cell.

The next step, which is the assembly of the notional haplotype, will now be discussed in more detail.

Assembling a Notional Haplotype

To detect and characterise the presence of chromosomes of paternal or maternal origin the next step is to assemble a notional haplotype of each chromosome. It is termed 'notional' herein since it is inferred rather than determined directly, and in certain embodiments the notional haplotype of say, a given chromosome of paternal original, may be characterised in subsequent steps of the method as arising from two copies of that chromosome of paternal original (in cases of trisomy, for example).

This notional haplotype may be assembled using particular sub-sets of SNPs as follows:

Assuming random SNP alleles for each parental chromosome, there are 16 different combinations of the four parental alleles for each SNP (Table 1).

Based on the haplotypes (i.e. the sequence of SNP alleles) of each parental chromosome, eight of these combinations can be predicted to result in genotypes in the test DNA that positively identify the presence of one out of the four parental chromosomes at that position ('informative') and four others will, dependent on results, either identify a pair of chromosomes one from each parent ('informative') or identify two possible combinations of parental chromosomes, out of the four possible pair-wise combinations ('semi-informative').

Therefore in one embodiment of the invention the notional SNP haplotype of the target cell chromosomes of paternal origin and of maternal origin is assembled using:
(i) informative SNP alleles that positively identify which one of the four paternal and maternal chromosomes, a chromosome in the target cell has originated from, or positively identify which paternal chromosome and which maternal chromosome a pair of chromosomes in the target cell have originated from, and optionally
(ii) semi-informative SNP alleles that positively identify which of two possible combinations of the four possible pair-wise combinations of paternal and maternal chromosomes, a pair of chromosomes in the target cell has originated from.

Characterising Target Cell Chromosomal Origin

In one embodiment of the invention step (c) is performed as follows:
(c1) assessing the notional SNP haplotype of target cell chromosomes of paternal origin and of maternal origin and thereby assigning each chromosome as absent, non-recombinant, recombinant, or present in 2 or more copies,
(c2) deducing aneuploidy of the chromosome in the target cell wherein step (c1) indicates an imbalance of chromosomes of paternal origin and of maternal origin, Once the notional haplotype is compiled, the relevant chromosome may be assigned as non-recombinant or recombinant as follows:

Non-recombinant chromosome: the SNP alleles will be identical to one of the parental chromosomes along the whole length of the chromosome. Therefore wherever there is an informative combination of SNP genotypes in the parents for that particular chromosome, the results will be positive whereas, and equally significantly, at SNPs informative for the other chromosome the results will be negative. Semi-informative SNPs will give results consistent with the presence of that particular parental chromosome (see FIG. 2(a)).

Thus in one embodiment a chromosome in the target cell is identified as non-recombinant wherein the results of its notional SNP haplotype are consistent with:
(i) its SNP alleles being identical to the SNP alleles of one of the two paternal chromosomes or one of the two maternal chromosomes along the length of the chromosome, and
(ii) an absence of the SNP alleles of the alternative of the two paternal or maternal chromosomes.

Recombinant chromosomes: with recombinant chromosomes, the pattern will be as for non-recombinant chromosomes except that there may be one or more alternating segments of both that parents chromosomes resulting from single, double or higher order recombination between the original parental chromosomes during the first meiotic division (see FIG. 2 (a)).

In performing the present invention, consideration is given to the fact that where successive informative or semi-informative SNPs indicate a switch from identifying one parental chromosome to the other (an apparent crossover event) this could be because of (1) an actual crossover during meiosis (i.e. normal recombination, as referred to above), (2) the presence of a second parental chromosome (trisomy, as discussed hereinafter), or (3) a SNP genotyping error.

Considering SNP genotyping error, as genome wide SNP genotyping methods are designed to reduce errors to a minimum, in any given instance a crossover event will be the most likely alternative since there is normally at least one crossover per chromosome arm. A long succession of informative and semi-informative SNP results consistent with that chromosome and not the other parental chromosome would therefore suggest normal recombination (see FIG. 2).

Therefore in one embodiment, a chromosome in the target cell is identified as recombinant wherein the results of its notional SNP haplotype correspond to SNP alleles of both of the two paternal chromosomes or two maternal chromosomes in one or more alternating segments consistent with normal recombination between the two chromosomes.

It is known that normal recombination will depend on (1) average, sex and chromosome specific data for the number of recombinations, and (2) interference between chiasmata preventing multiple recombination events over short distances.

Figure 3:
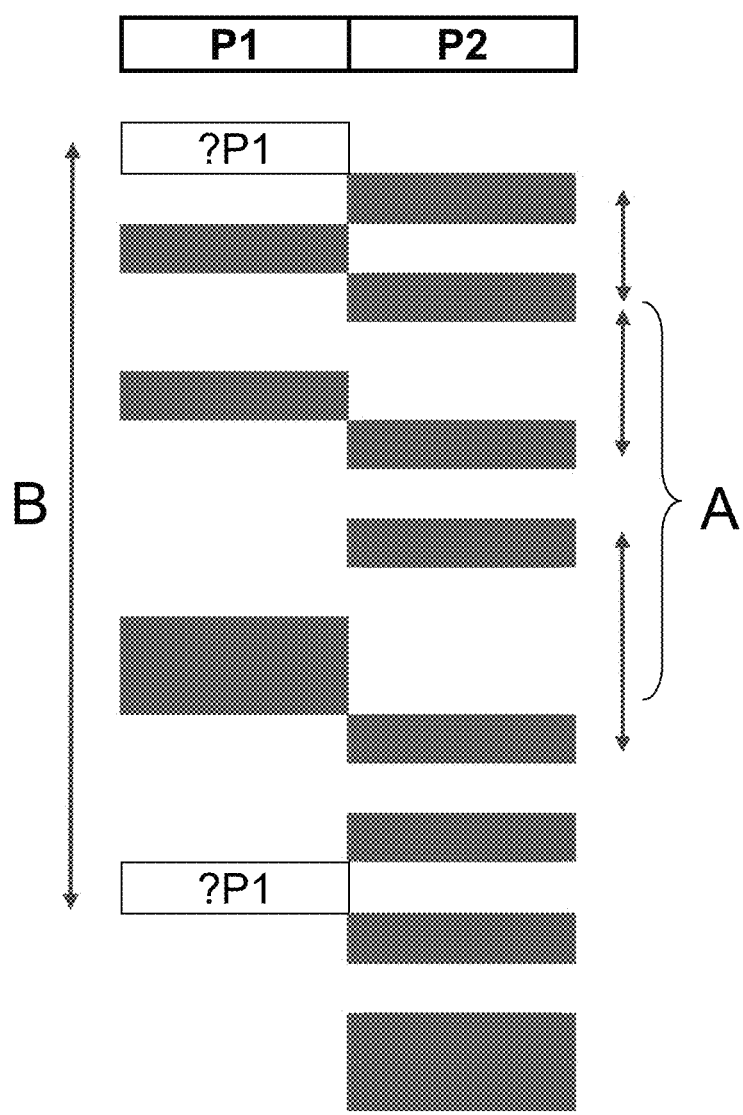
Figures 1, 4:
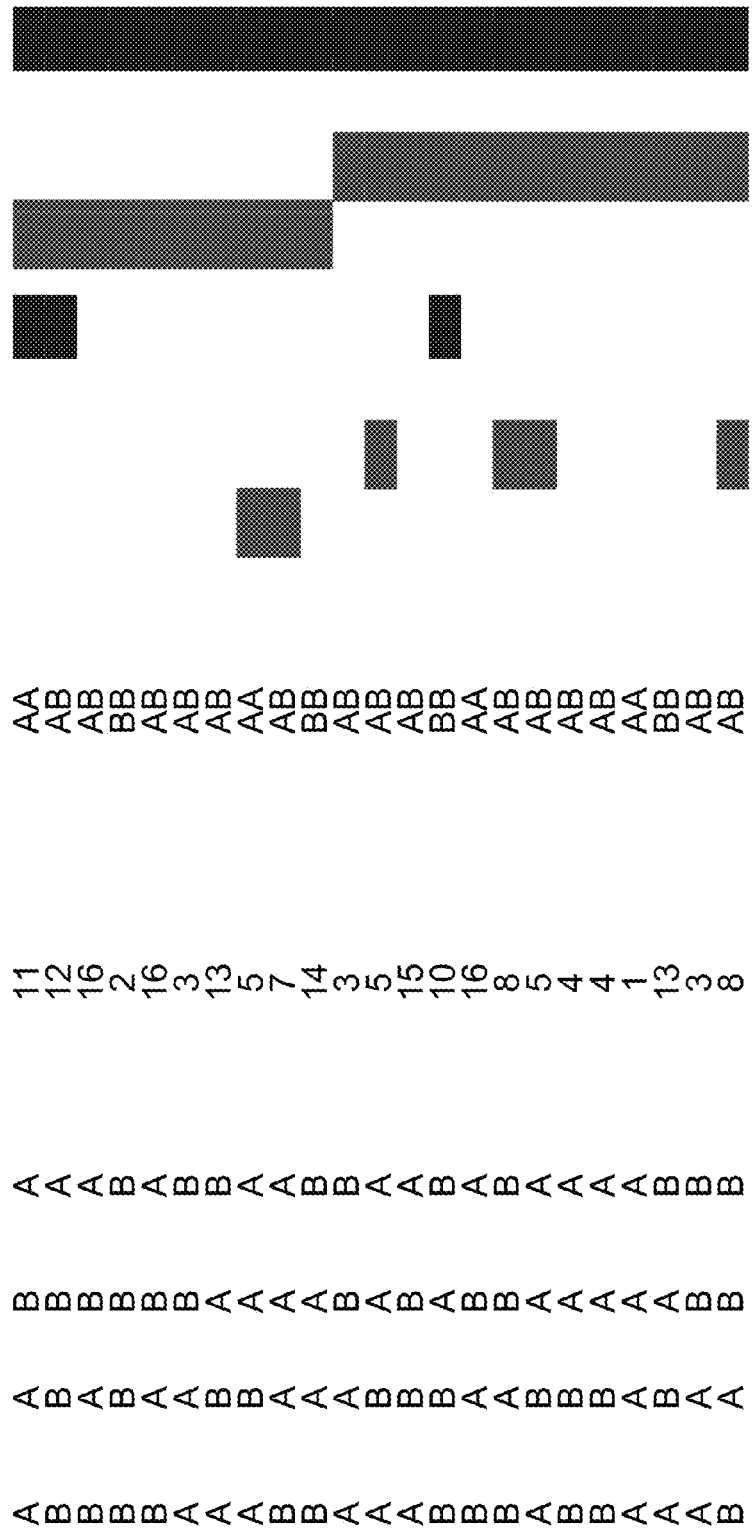
Figures 3, 4:
Figure 4:
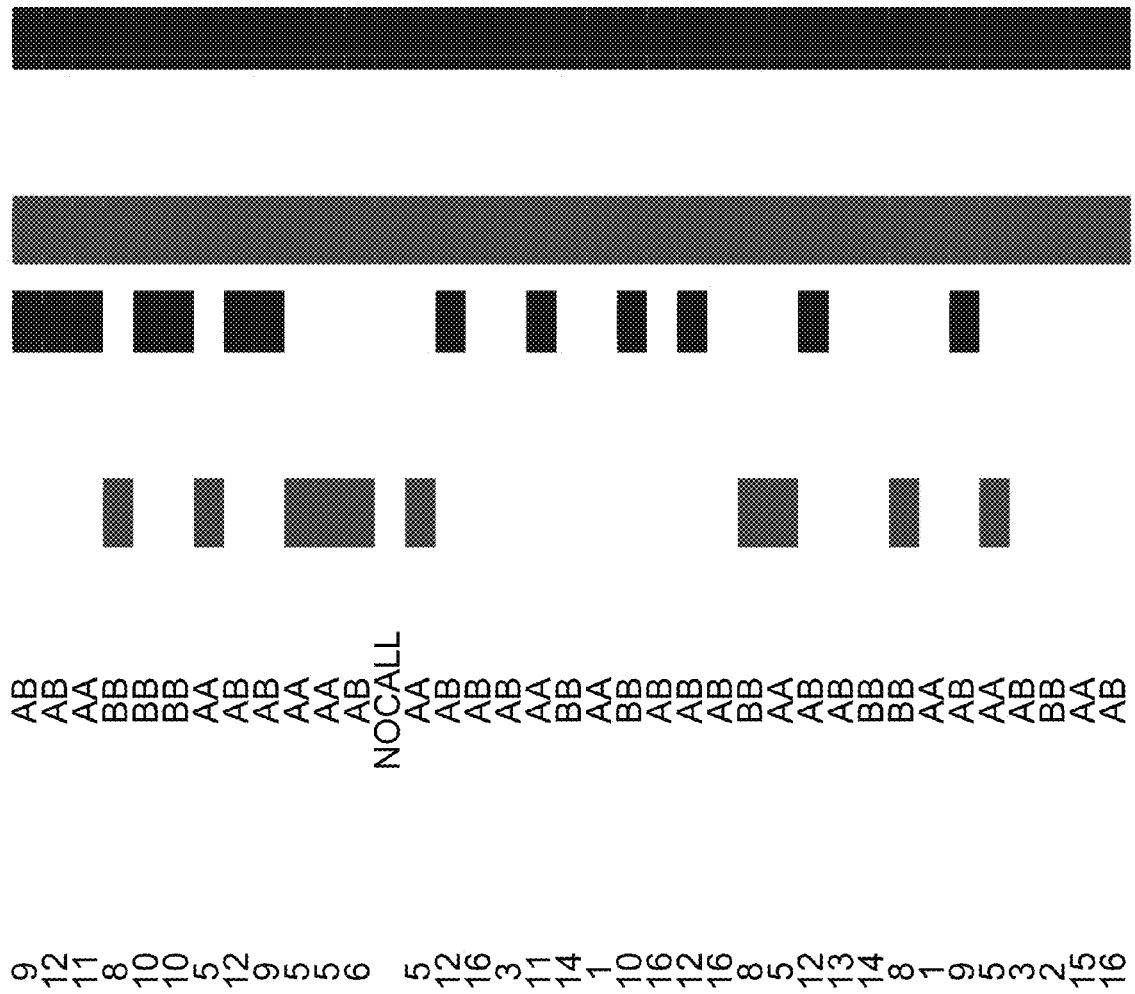

Therefore in one embodiment, consistency with normal recombination is assessed based on the statistical likelihood of normal recombination between particular adjacent, informative SNP alleles of the two paternal chromosomes or two maternal chromosomes during the first meiotic division. Preferably the statistical likelihood is assessed based on is one or more of the following criteria:

(i) the average number of recombination events for the specific paternal or maternal chromosome, (ii) the position of the apparent recombination events on each chromosome arm relative to each other, the centromere and the telomere ie the ends of the chromosome arm involved Multiple chromosomes: if successive informative and semi-informative SNPs alternate repeatedly and\or apparently randomly between the two parental chromosomes, it is highly likely that the test DNA is trisomic rather than a series of double crossover or recombination events (FIG. 3; FIG. 4).

This is because the pattern of normal recombination is non-random and specifically the presence of one crossover physically inhibits another crossover nearby, a phenomenon known as crossover interference (Broman and Weber, 2000).

With two non-recombinant chromosomes from one parent the SNP notional haplotype result will alternate all along the chromosome. With other combinations of non-recombinant and recombinant chromosomes, the two parental haplotypes will be detectable for a segment of the chromosome which shows the repetitive, apparently random, alternation.

In terms of the frequencies of 'normal' alternating segments, based on a large experimental data set, Broman and Weber (2000) propose that the probability of a double crossover between two non-recombinant informative polymorphisms can be estimated according to the formula:

$$p=(0.0114d-0.0154)^4$$

where p is the probability of a double crossover in an interval d measured as genetic distance in centiMorgans (cM) between non-recombinant loci.

The probability that one SNP, indicating the presence of the other parental chromosome (or >1 informative SNP with no intervening contradictory informative SNPs) is the result of a double crossover is therefore defined by the probability between adjacent flanking SNPs informative for that chromosome (FIG. 2).

Thus in one embodiment the statistical likelihood of a double crossover between two SNP alleles is calculated according to the formula:

$$p=(0.0114d-0.0154)^4$$

where p is the probability of a double crossover in an interval d measured as genetic distance in centiMorgans (cM) between the SNP alleles.

As an example of the operation of this formula, for an average spacing of 0.32 cM (as with the Affymetrix GeneChip 10K system) and n SNPs:

| N | d (cM) | p |
|---|---|---|
| 10 | 3.2 | $1.6 \cdot 10^{-7}$ |
| 50 | 16 | $8.35 \cdot 10^{-4}$ |
| 100 | 32 | 0.015 |
| 200 | 64 | 0.254 |

Thus in most cases, the probability of a pattern alternating between the haplotypes of both chromosomes from one parent at successive informative and semi-informative SNPs will be very low particularly where the density of SNPs analysed is high and generally much lower than the possibility of genotyping error.

The probability of trisomy is further increased with the number and extent of this alternating pattern which will depend on the number and position of true crossover events on both of the chromosomes.

In addition to the number of apparent crossovers in the notional haplotypes, several other assumptions about the number and distribution of crossovers across the genome (Lynn et al, 2004) may be used in assigning the chromosome as likely recombinant or not:

Direct counts of the number of chiasmata indicate that the average total number in males is 50.6 (Hulten, 1974) and in females 70 (Hulten and Tease, 2003; Tease and Hulten, 2004).

Average number of crossovers on individual chromosomes.

Distribution of crossovers on individual chromosomes.

Density and Nature of SNPs

Across the whole genome when analysing, for example, 10K SNPs, despite the high accuracy rate, one or more random genotyping errors causing isolated individual positive results at informative SNPs for the second parental chromosome may occur.

Therefore in preferred embodiments a threshold number of positive and negative informative and semi-informative SNPs is set.

In one embodiment at least 5000 and/or 2500 informative and/or semi-informative SNP alleles, respectively, distributed across the whole genome are used to assemble the notional SNP haplotype of target cell chromosomes of paternal origin and of maternal origin. However for individual chromosomes a less number may be sufficient—this can be assessed by those skilled in the art according to the preferred method of typing and the accuracy associated with it and with any optional method of amplification employed.

In one embodiment the average distance between the interrogated SNPs is less than 0.1, 0.2, 0.3, 0.4 or 0.5 kb.

In one embodiment the average distance between the interrogated SNPs is less than 0.1, 0.2, 0.3, 0.4 or 0.5 cM Because of allele dropout (ADO), ie the random failure to amplify one of the parental alleles, when amplifying the DNA from single or small numbers of cells for application in preimplantation genetic diagnosis, SNP genotype analysis may preferably be based in whole or in part on those results giving a heterozygous result at an informative or semi-informative SNP. Thus in one embodiment at least 2500 heterozygous informative SNP alleles ("AB" in Table 1) are used to assemble the notional SNP haplotype of target cell chromosomes of paternal origin and of maternal origin.

Karyotyping

As noted above, aneuploidy of the chromosome in the target cell is detected wherein the notional haplotype indicates an imbalance of chromosomes of paternal origin and of is maternal origin. Details of the detection strategies of different aneuploidies are as follows:

In one embodiment where the notional SNP haplotype of target cell chromosomes indicates the presence of one chromosome of paternal origin and one chromosome of maternal origin and the cell is deduced to be normal diploid in respect of the relevant chromosome.

Nullsomy: In one embodiment, where the notional SNP haplotype of target cell chromosomes indicates an absence of any chromosome or chromosome segment of paternal origin and maternal origin, the cell is deduced to be nullsomic for the relevant chromosome or chromosome segment.

Monosomy: Here, there will be only one chromosome from one parent, but it can be either non-recombinant or recombinant. Monosomy will therefore be detected in two ways (1) apparent homozygosity (either 'AA' or 'BB' and not 'AB') for all SNPs along the chromosome, and (2) identity to the haplotype for one of the parental chromosomes (non-recombinant) or an alternating pattern between the two haplotypes from one parent (consistent with normal recombination between the two chromosomes). Thus in one embodiment, where the notional SNP haplotype of the target cell chromosomes indicates an absence of a chromosome or chromosome segment of either paternal origin or maternal origin but not both, the cell is deduced to be monosomic for the relevant chromosome or chromosome segment.

Monosomies may be detected whether they arise before or after fertilisation.

Trisomy: As discussed above, where the notional SNP haplotype of target cell chromosomes indicates the presence of both of the two paternal chromosomes or two maternal chromosomes in a pattern and\or frequency inconsistent with normal recombination between the two chromosomes, the cell is deduced to be trisomic for all or part of the relevant chromosome or chromosome segment.

Specifically the method is adapted to detect trisomy where paired chromosomes in each of the paternal or maternal cells differ (which is commonly the case), and where the two chromosomes of paternal or maternal origin in the target cell differ over all or part of the chromosome (which would apply to the majority of trisomies i.e. most of those arising during meiosis—see FIG. 1(b))) and informative and semi-informative SNPs appear and are interrogated in the regions which differ (which would typically apply where sufficient density of SNPs are assessed).

It therefore provides a useful tool in detecting aneuploidy in these common situations. Having described certain embodiments of the invention above, some particular modes of operation will now be discussed.

Combined and Multiple Detection Strategies

If desired, the invention may be combined with one or more other karyotyping strategies.

For example a further step may include quantitation of alleles to increase the accuracy and resolution of trisomy detection i.e. in one embodiment the method further comprises confirming the deduction by quantifying the SNPs across the chromosome of the target cell (Meng et al., 2005).

In one embodiment the method further comprises diagnosing the presence of an inherited genetic disease in the target cell by comparing the notional SNP haplotype of the target cell with the SNP alleles of the paternal chromosomes and the maternal chromosomes and one or more affected siblings to diagnose the disease in the target cell by linkage. Linkage is a method in which instead of detecting a disease-causing gene mutation itself, one or more informative markers such as STRs or SNPs, either close to or within the affected gene, are used to track the affected copy of the gene by comparison with the markers inherited by an affected child (Abou-Sleiman et al, 2002). With genome wide SNP analysis of the target cell genotype as discussed above, multiple closely linked SNPs flanking the affected gene may be analysed permitting highly accurate linkage analysis.

In one embodiment the method further comprises diagnosing the presence of a susceptibility to a common disease or cancer in the target cell by comparing the notional SNP haplotype with a haplotype known to be associated with said disease. Such associations are being increasingly established, for example via the "International HapMap Consortium" which is mapping genome wide variation in SNP haplotypes in the human population, is to facilitate disease association studies (International HapMap Consortium, 2005). The associations do not per se form part of the invention, but the combination of this haplotype analysis with the karyotyping method described herein forms one aspect of the invention.

Paternal and Maternal Cells and Chromosomal Haplotypes

In one embodiment paternal and maternal cells are provided from blood or buccal cavity Analysis of SNPs from related individuals across at least one generation allows the identification of a haplotype for each chromosome in positions where the alleles are different. Specifically, the haplotype of SNP alleles can be ascertained by analysing the DNA of each parent and comparing the results with a haploid gamete, child or parent or a combination of these. Those skilled in the art are aware of numerous algorithms and related software programmes that allow the haplotypes to be inferred from analysis of diploid individuals e.g. PHASE (Stephens and Donnelly, 2003) and SIMHAP (www.genepi.com.au/simhap).

In one embodiment SNP haplotype of paternal and maternal chromosomes is derived from analysis of the SNP haplotype of cells removed from sibling fertilized embryos following in vitro fertilisation (IVF) following whole genome amplification.

In one embodiment SNP haplotype of paternal and maternal chromosomes is derived from analysis of multiple single parental haploid gametes following whole genome amplification.

Where two chromosomes or chromosome segments from one parent are shown to be identical, the method will not be applicable for that chromosome or segment and alternative methods should be used.

Target Cells

In one embodiment the target cell has been provided from a mammalian embryo which has resulted from IVF. In one embodiment the embryo is a pre-implantation embryo (see e.g. Handyside et al, 2004).

Where the invention is applied to animals such as livestock, the embryo may be recovered from the uterus.

In one embodiment the target cell(s) have been provided from a fetus

In one embodiment a number equal to, or at least, 1, 2, 3, 4, or 5 cells are provided In one embodiment SNP interrogation is preceded by whole genome amplification In one embodiment the whole genome amplification employs isothermal Multiple Displacement Amplification (MDA) which permits whole genome amplification using the bacteriophage phi29 polymerase for amplification from small numbers of cells (see e.g. Handyside et al, 2004).

Interrogation of SNPs

Preferred markers are biallelic SNPs, which occur throughout the genome (~10 million per genome, wherein the SNP is defined as >1% variation between individuals in a population).

Various methods for large scale single nucleotide polymorphism (SNP) analysis exist (see Syvanen, 2005, especially Table 1). These include SNPstream (Bell, P. A. et al. SNPstream UHT: ultra-high throughput SNP genotyping for pharmacogenomics and drug discovery. *Biotechniques* Suppl., 70-72, 74, 76-77 (2002)); Genorama, APEX (Kurg, A. et al. Arrayed primer extension: solid-phase four-colour DNA resequencing and mutation detection technology. *Genet. Test.* 4, 1-7 (2000)); GeneChip 100K (Matsuzaki, H. et al. Genotyping over 100,000 SNPs on a pair of oligonucleotide arrays. *Nat. Methods* 1, 109-111 (2004)); Perlegen wafers (Hinds, D. A. et al. Whole-genome patterns of common DNA variation in three human populations. *Science* 307, 1072-1079 (2005)); Molecular Inversion Probes (Hardenbol, P. et al. Highly multiplexed molecular inversion probe genotyping: Over 10,000 targeted SNPs genotyped in a single tube assay. *Genome Res.* 15, 269-275 (2005)); GoldenGate Assay (Fan, J. B. et al. Highly parallel SNP genotyping. *Cold Spring Harb. Symp. On Quant. Biol.* LXVII, 69-78 (2003)). Other methods include the Illumina "BeadArray".

A preferred embodiment employs the Affymetrix GeneChip™ 10K Microarray is designed to analyse 10,000 distributed at an average distance of 0.2 Kb across each of 22 chromosomes (see Matsuzaki, H. et al. Parallel genotyping of over 10,000 SNPs using a one-primer assay on a high-density oligonucleotide array. *Genome Res.* 14, 414-425 (2004))

In the case of oligonucleotide chips, the oligonucleotides that can be bonded to a chip according to the invention will be capable of distinguishing biallelic SNPs across the genome. Preferred are 25 nucleotide-long oligonucleotides.

Thus in one embodiment the SNPs are interrogated on a "gene" or "oligonucleotide" chip or microarray. As is well known in the art these are miniaturized vehicles, in most cases made of glass or silicon, on whose surface oligonucleotides of known sequence are immobilized in an ordered grid of high density.

Another preferred embodiment employs the Illumina's "infinium"™ Human-1 BeadChip. This system may enable whole-genome genotyping of over 100,000 SNP markers, 70% of which are located in exons or within 10 kb of transcripts (see e.g. *Pharmacogenomics* (2005) 6(7), 777-782). The system is based on the random assembly of derivatized microscopic beads approximately 3 µm in size) into wells of a patterned substrate, and may permit specified combinations of SNPs to be interrogated.

Systems

Preferably a system for use in the present invention would comprises means for SNP interrogation plus a programmed storage device or medium for causing a computer to analyse the resulting data. The SNP interrogation data could be stored for later analysis or analysed 'on the fly'—as used herein the term "database" covers both types of data source.

Preferred means for SNP interrogation would be an oligonucleeotide chip which would interrogate at least the preferred chromosomes at the appropriate density discussed above. Preferably it would include the whole genome.

Thus preferred means for SNP interrogation would include:
(i) A high density of biallelic SNPs on chromosomes frequently associated with miscarriage or viable abnormal pregnancies (X, Y, 22, 21, 18, 16, 13). The means may interrogate a full polymorphic set on these chromosomes.
(ii) SNPs which are highly heterozygous in the general population increasing their informativeness,
(iii) Relatively increased density in all the known microdeletion syndrome regions,
(iv) Relatively increased density in regions associated with common single gene defects,
(v) Known SNP 'haplotags' associated with predisposition to common complex diseases.

The present invention may be implemented with a computer. Typically this would include a central processing unit (CPU) connected by a system bus or other connecting means to a communication interface, system memory (RAM), non-volatile memory (ROM), and one or more other storage devices such as a hard disk drive, a diskette drive, and a CD ROM drive.

The computer also includes a display device, such as a printer, CRT monitor or an LCD display, and an input device, such as a keyboard, mouse, pen, touch-screen, or voice activation system. The input device may receive data directly from the means for SNP interrogation via an interface (as for example with the Affymetrix system).

The computer stores and executes various programs such as an operating system and application programs.

The computer-usable medium would cause the computer to analyse haplotypes and perform molecular karyotyping to assign parental origin along the length of each chromosome, and report on aneuploidy where this was detected. The medium may for example be selected from the group consisting of a hard disk a floppy disk, Random Access Memory, Read Only Memory and Electrically Eraseable Programable Read Only Memory.

Thus the invention provides a computer-usable medium having computer-readable program code or instructions stored thereon (i.e. a programmed storage device) for causing a computer to execute a method to determine aneuploidy or chromosomal recombination in a target cell, the method being any one of those discussed herein.

Preferably the method comprises:
(a) accessing a database comprising genotype data obtained from a plurality of closely adjacent biallelic SNP loci present in a chromosome of the target cell,
(b) accessing a database comprising SNP haplotype data of the corresponding paternal is and maternal chromosomes (i.e. 'P1', 'P2', 'M1'; 'M2'),
(c) comparing target cell SNP data from the database of step (a) with SNP haplotype data from the database of step (b) to assemble a notional haplotype of regions of the target cell chromosomes of paternal origin and of maternal origin,
(d) assessing the notional SNP haplotype of target cell chromosomes of paternal origin and of maternal origin to detect aneuploidy or chromosomal recombination of the chromosome in the target cell.

Optionally, each SNP locus of the 'x' SNPs of the database in step (b) is assigned a value 'n' in accordance with which of the 16 combinations of four parental SNP alleles is present at that locus, and wherein step (c) comprises assembling a notional haplotype at that locus by comparing
(i) the genotype data for the biallelic SNP at that locus from the database of step (a) and,
(ii) the value 'n' at that locus from the database of step (b) with,
(iii) a chromosomal origin table,
and thereby assigning the SNP locus of the target cell chromosomes as originating from a paternal or maternal chromosome.

By 'chromosomal origin table' is meant a reference set of data by which the chromosomal origin (e.g. 'P1', 'P2', 'M1; or 'M2') can be assigned at that locus based on the values at (i) and (ii). This may correspond to that given in Table 1, last column.

Preferably the notional SNP haplotype of regions of the target cell chromosomes of paternal origin and of maternal origin is assembled using a subset of the 'x' SNP loci from the database in step (b), which subset consists of:
(i) informative SNP alleles that positively identify which one of the four paternal and maternal chromosomes, a chromosome in the target cell has originated from, or positively identify which paternal chromosome and which maternal chromosome a pair of chromosomes in the target cell have originated from, and optionally
(ii) semi-informative SNP alleles that positively identify which of two possible combinations of the four possible pair-wise combinations of paternal and maternal chromosomes, a pair of chromosomes in the target cell has originated from.

Optionally the subset may consist of heterozygous informative SNP alleles.

Optionally the method may comprises storing the notional haplotype result obtained for each SNP locus of the 'x' SNPs, or a subset thereof.

An example of software (Excel Visual Basic for Applications (VBA) code I) is listed in Appendix 1, and this identifies the different combinations of parental alleles at each SNP and assigns parental origin at informative SNP loci. FIG. 4 shows resulting notional haplotypes and the actual target cell haplotypes as determined independently.

The program may identify the chromosome in the target cell as non-recombinant wherein the results of its notional SNP haplotype are consistent with:
(i) its SNP alleles being identical to the SNP alleles of one of the two paternal chromosomes or one of the two maternal chromosomes along the length of the chromosome, and
(ii) an absence of the SNP alleles of the alternative of the two paternal or maternal chromosomes.

The program may identify the chromosome in the target cell as recombinant wherein the results of its notional SNP haplotype correspond to SNP alleles of both of the two paternal chromosomes or two maternal chromosomes in one or more alternating segments consistent with normal recombination between the two chromosomes.

The program may identify the chromosome in the target cell as trisomic for the chromosome where the notional SNP haplotype of the target cell chromosome indicates the presence of both of the two paternal chromosomes or two maternal chromosomes in a pattern and\or frequency inconsistent with normal recombination between the two chromosomes The program may statistically analyze the likelihood of normal recombination between the SNP loci based on one or more of the following criteria:
(i) a database the average number of recombination events for the specific paternal or maternal chromosome,
(ii) the position of the apparent recombination events on each chromosome arm relative to each other, the centromere and the telomere Optionally the program may calculate a numerical measure of probability of, for example, trisomy based on this frequency and pattern data.

The program may identify the chromosome in the target cell as nullsomic for the chromosome where the notional SNP haplotype of target cell chromosome indicates an absence of the chromosome or a segment thereof of both paternal origin and maternal origin.

The program may identify the chromosome in the target cell as monosomic for the chromosome where the notional SNP haplotype of the target cell chromosome indicates an absence of the chromosome or a segment thereof of paternal origin and maternal origin but not both.

Optionally a threshold number of positive and negative informative and optionally semi-informative SNPs is set, and a karyotype is determined only when this number is exceeded.

The invention also provides a computer programmed to execute a method as described above.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

FIGURES

The patent or application file contains at least one drawing executed in color. Copies of this patent or patent application publication with color drawings will be provided by the Office upon request and payment of the necessary fee.

FIG. 1(a): schematic showing normal meiosis I and II

Figure 2A:
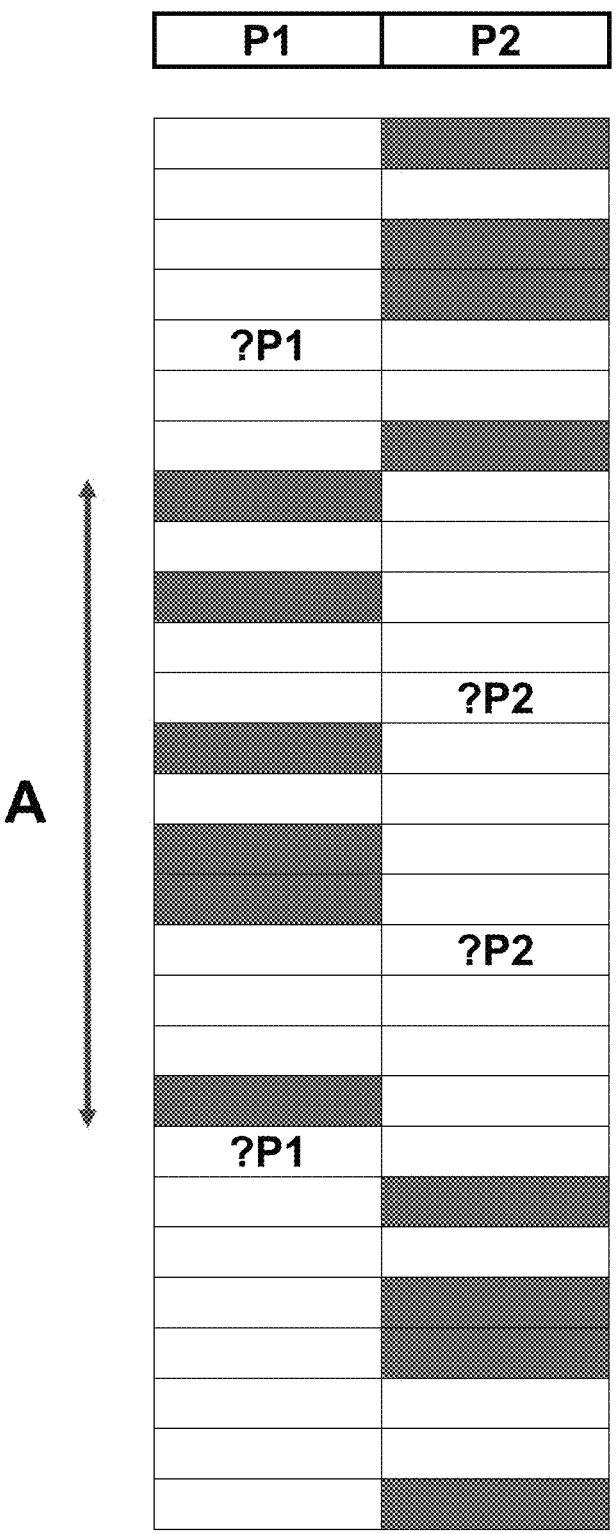
Figure 2B:
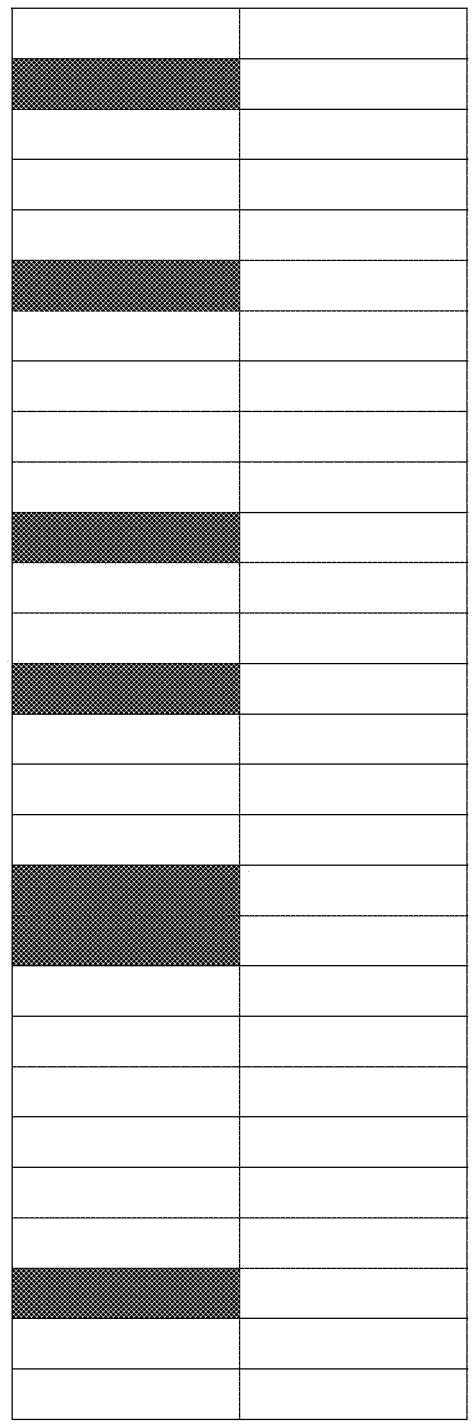

FIG. 1(b): schematic showing non-disjunction during meiosis leading to aneuploidy FIG. 2: schematic representation of SNP genotype analysis for a chromosome pair in test DNA from a fetus or embryo. Each row represents a SNP locus and each column, the haplotypes for the two paternal chromosomes (P1 and P2) and two maternal chromosomes (M1 and M2). A positive result at an informative SNP is shaded. A negative result at an informative SNP is marked with ?PX (?MX omitted for clarity). In FIG. 2(a) the segment marked A of the paternal copy of the chromosome is identified as a double recombinant because multiple consecutive informative SNPs positively identify the haplotype of P1 and others informative for P2 are negative. The length of the chromosomal segment and number of crossovers both for this chromosome and overall would also be taken into account and because of crossover interference would normally extend over a greater number of SNPs than in this diagrammatic representation. In FIG. 2(b) The maternal chromosome is non-recombinant in this region and only SNPs informative for M1 are positive.

FIG. 3: Schematic representation of SNP genotype analysis for a chromosome pair in test DNA from a fetus or embryo as described in FIG. 2. In this example, the segment marked B is assigned as trisomic because of the positive result for multiple alternating SNPs informative for both chromosomes. The probability of each individual positive result for P1 being a double recombinant between flanking positive results for P2 (marked A) is very small given the average genetic distance between SNPs when using high density SNP analysis.

FIG. 4: Parental and test offspring genotype data analysed using the Excel VBA code in Appendix 1 illustrating how informative combinations of biallelic SNPs allow identification the parental origin along a chromosome.

Figures 4, 5:
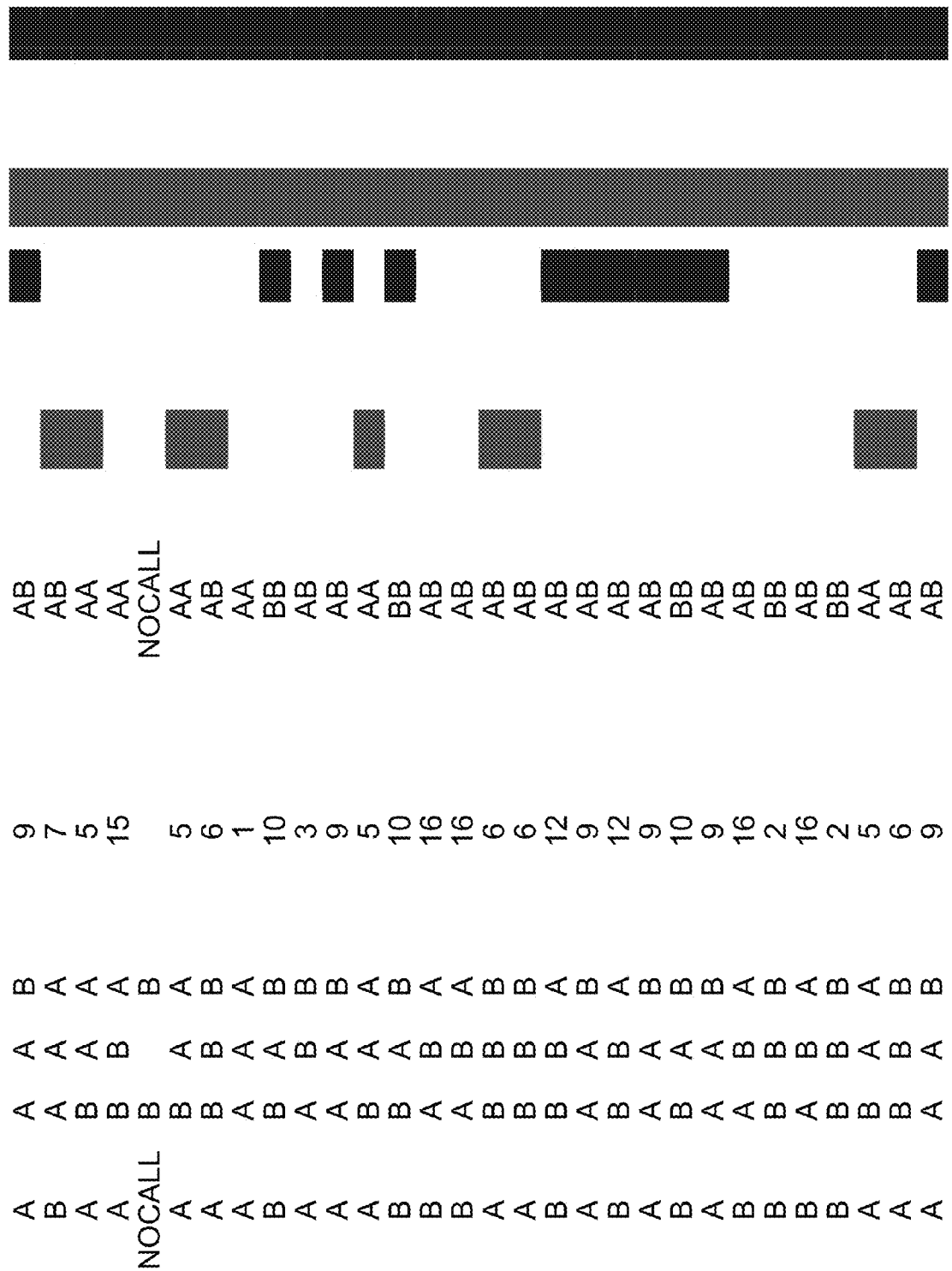
Figures 4, 5, 6:
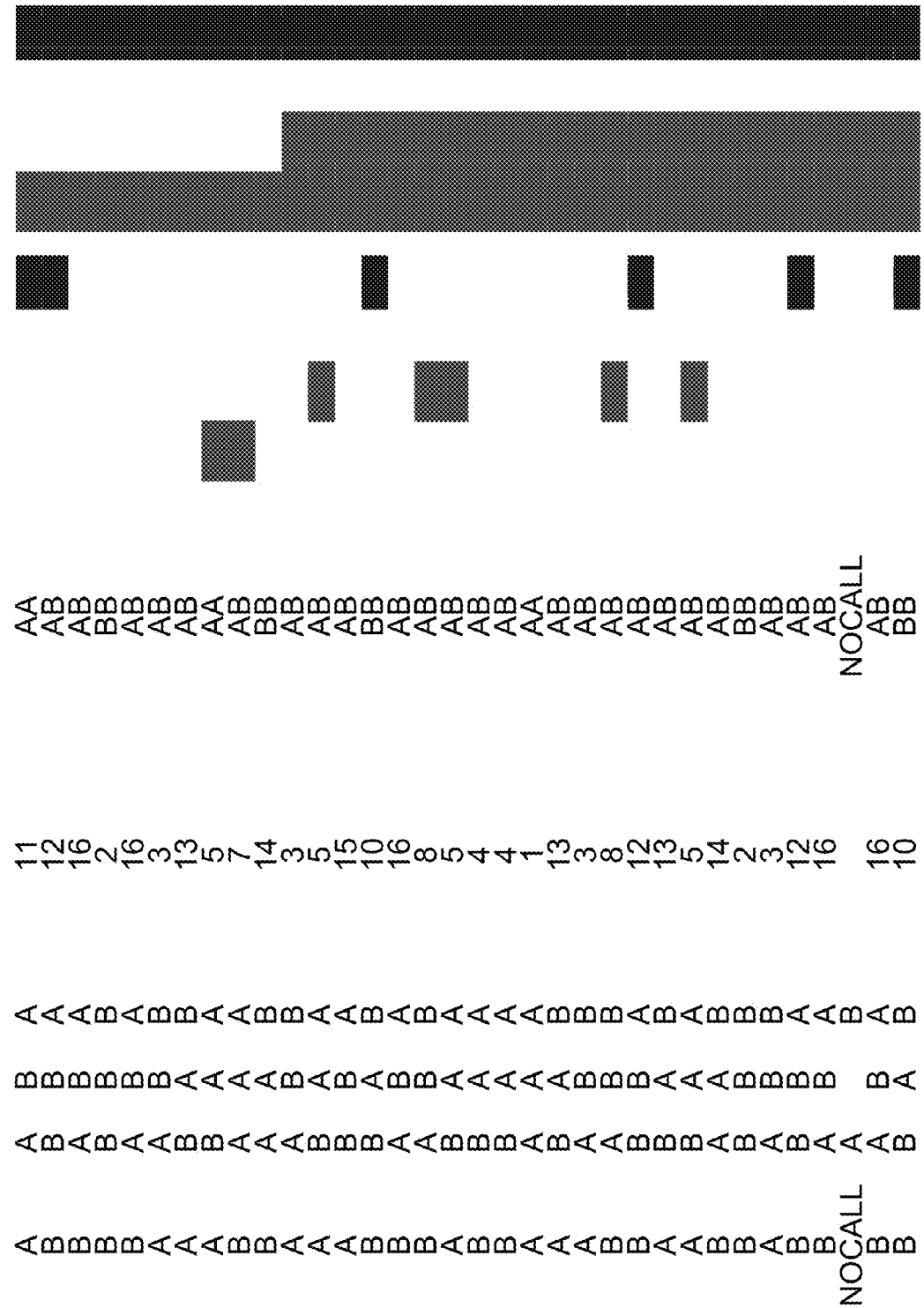
Figures 4, 5, 6, 7:
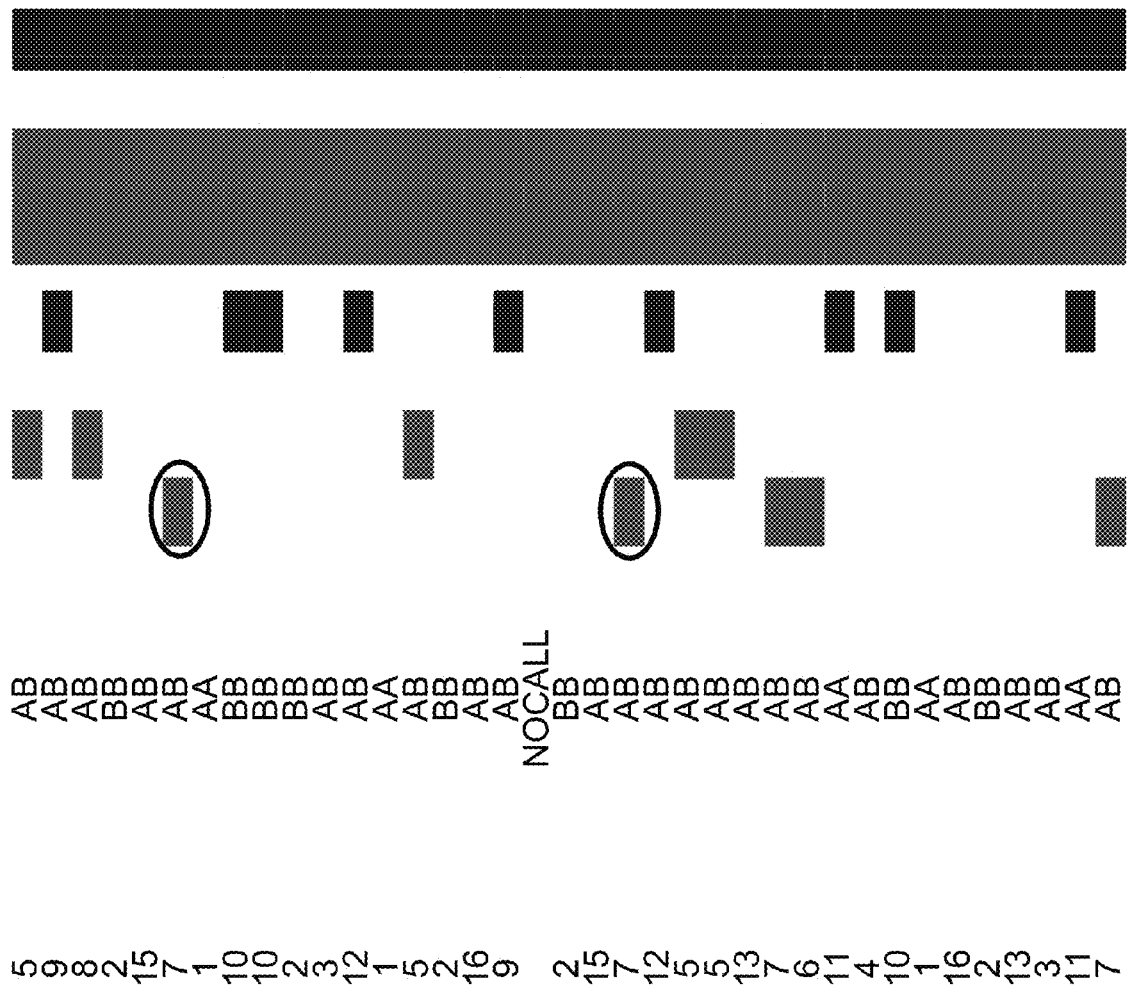
Figures 4, 5, 6, 7, 8, 9, 10:

FIG. 5: Flowchart illustrating the present invention with multiple detection strategies.

EXAMPLES

Example 1

Theoretical Background

During meiosis and the formation of gametes, homologous chromosomes pair and recombine resulting in four chromosomes, which on average will consist of two non-recombinant and two recombinant chromosomes. Each of the resulting chromosomes therefore now has a unique SNP haplotype.

Following fertilisation, each embryo has a unique combination of haplotypes from the non-recombinant or recombinant chromosomes segregated to the two gametes from the two parents. In euploid embryos, with the normal pairs of each chromosome, each chromosome will have a distinct haplotype and the parental origin of each chromosome will be identifiable from the non-recombinant or unique recombinant haplotype. Similarly, trisomy and monosomy will also be detectable.

Table 1 below shows how SNPs can be classified as informative, semi-informative, or non-informative.

TABLE 1

The 16 combinations of parental SNP haplotypes based on a random distribution of alleles. Informative combinations identify a parental haplotype irrespective of the result. Informative/semi-informative combinations of alleles identify one of both parents chromosomes or two possible combinations depending on the genotype of the DNA being tested.

| Informativity | # | P1 | P2 | M1 | M2 | Test genotype |
|---|---|---|---|---|---|---|
| Non-informative | 1 | A | A | A | A | PA |
|  | 2 | B | B | B | B | BB |
|  | 3 | A | A | B | B | AB |
|  | 4 | B | B | A | A | AB |
| Informative (all results identify presence of 1 parental chromosome) | 5 | A | B | B | B | AB = P1<br>BB = P2 |
|  | 6 | B | A | B | B | AB = P2<br>BB = P1 |
|  | 7 | B | B | A | B | AB = M1<br>BB = M2 |
|  | 8 | B | B | B | A | AB = M2<br>BB = M1 |
|  | 9 | B | A | A | A | AB = P1<br>AA = P2 |
|  | 10 | A | B | A | A | AB = P2<br>AA = P1 |
|  | 11 | A | A | B | A | AB = M1<br>AA = M2 |
|  | 12 | A | A | A | B | AB = M2<br>AA = M1 |
| Informative/semi-informative (⅔ possible results identify a pair of parental chromosomes and ⅓ results could be either of two combinations) | 13 | A | B | A | B | AA = P1M1<br>BB = P2M2<br>AB = P1M2<br>or P2M1 |
|  | 14 | B | A | B | A | AA = P2M2<br>BB = P1M1<br>AB = P2M1<br>or P1M2 |
|  | 15 | A | B | B | A | AA = P1M2<br>BB = P2M1<br>AB = P1M1<br>or P2M2 |
|  | 16 | B | A | A | B | AA = P2M1<br>BB = P1M2<br>AB = P2M2<br>or P1M1 |

Example 2

Informativity of SNPs and ADO

In some embodiments when DNA is amplified from single cells, for example, for preimplantation genetic diagnosis (PGD), one of the parental alleles may fail to amplify at random resulting in allele dropout (ADO). Table 2 below demonstrates that where ADO occurs at informative SNPs, half of these will be detected because the apparent test genotype is not possible and therefore the true heterozygous result ("AB") can be inferred.

TABLE 2

Effect of allele dropout (ADO) at informative SNPs

| Maternal (M) chr | | Paternal (P) chr | | Test genotype and chromosome identified |
|---|---|---|---|---|
| 1 | 2 | 1 | 2 | |
| B | A | A | A | AA = M2 AB = M1 M1 (BB = AB*) |
| A | B | A | A | AA = M1 AB = M2 (BB = AB*) |
| A | A | B | A | AA = P2 AB = P1 (BB = AB*) |
| A | A | A | B | AA = P1 AB = P2 (BB = AB*) |
| A | B | B | B | BB = M2 AB = M1 (AA = AB*) |
| B | A | B | B | BB = M1 AB = M2 (AA = AB*) |
| B | B | A | B | BB = P2 AB = P1 (AA = AB*) |
| B | B | B | A | BB = P1 AB = P2 (AA = AB*) |

*For this combination of parental SNPs, the test genotype cannot have two copies of this allele indicating allele dropout (ADO) i.e. failure to amplify one of the parental alleles at random. The test genotype can therefore be assumed to be AB. This approach increases the power of the test when the invention is used in single cell applications such as preimplantation genetic screening.

Example 3

Combined SNP Quantitative and Sequence Based Analysis

If relative quantitation of each SNP allele is achieved, the normal disomic genotype combinations, "AA", "AB" and "BB", are supplemented by "A" and "B" in monosomy and "AAA", "BBB", "AAB" and "ABB".

Table 3 demonstrates the extra information that is available by combining genotyping and quantitation of SNPs. While these possible combination of SNP alleles genotyping may be uninformative, quantitation would identify the chromosome as trisomic even though the parental origin is unknown in the first two examples.

TABLE 3

Combined genotyping and quantitation of SNPs

| Maternal (M) chr | | Paternal (P) chr | | Test genotype and chromosome |
|---|---|---|---|---|
| 1 | 2 | 1 | 2 | identified |
| A | A | A | A | AAA = Trisomic M1 M2 or P1 P2 |
| B | B | B | B | BBB = Trisomic M1 M2 or P1 P2 |
| A | A | B | B | AAB = M1 M2 P1 or P2<br>ABB = M1 or M2 P1 P2 |
| B | B | A | A | AAB = M1 or M2 P1 P2<br>BBA = M1 M2 P1 or P2 |
| A | B | A | B | AAB = M1 P1 + M2 or P2<br>ABB = M2 P2 + M1 or P1 |
| B | A | A | B | AAB = M2 P1 + M1 or P2<br>ABB = M1 P2 + M2 or P1 |
| A | B | B | A | AAB = M1 P2 + M2 or P1<br>BBA = M2 P1 + M1 or P2 |

TABLE 3-continued

Combined genotyping and quantitation of SNPs

| Maternal (M) chr | | Paternal (P) chr | | Test genotype and chromosome identified |
|---|---|---|---|---|
| 1 | 2 | 1 | 2 | |
| B | A | B | A | AAB = M2 P2 + M1 or P1<br>BBA = M1 P1 + M2 or P2 |

Example 4

Use of Multiple Displacement Amplification (MDA)

A Microsoft Excel VBA macro (SNP analysis (1)) to analyse these combinations of SNPs and test genotypes is set out below in Appendix 1.

The results are shown in FIG. 4. The data is test genotype analysis of SNPs across chromosome 21. Maternal and paternal haplotypes have been created based on an individual genotyped using the Affymetrix GeneChip 10K microarray. At some SNPs the alleles could not be reliably identified ("No call"). Otherwise, for illustration purposes, the test genotype is assumed to be 100% accurate and is based on the actual test haplotypes shown. The numbered parental haplotype combinations are as defined in Table 1. In this example only fully informative SNPs combinations (5-12) have been used to identify the test haplotypes. In addition, semi-informative combinations would be used and the information further analysed to distinguish double recombination from trisomy or genotyping errors. Two examples are shown—one normal disomic and one trisomic for chromosome 21. The black circles indicate the critical SNP results that indicate this test sample is trisomic i.e. they demonstrate the presence of alternating segments which are not consistent with normal recombination between the two chromosomes.

Example 5

Prenatal Diagnosis Following CVS or Amniocentesis

Current methods of analysis for chromosomes include karyotyping, fluorescent in situ is hybridisation (FISH) for a restricted number of chromosome pairs or quantitative fluorescent PCR. SNP profiling according to the present invention combines detection of aneuploidy, deletions and unbalanced translocations.

Current methods for detection of single gene defects combine mutation detection (requiring identification of the mutation) and informative linked markers in some cases requiring prior linkage analysis and test development. Because of the density of SNPs analysable linkage to combinations of SNPs will also be possible in many cases.

Example 6

Preimplantation Genetic Diagnosis Following IVF

Preimplantation genetic diagnosis (PGD) requires analysis of single or small numbers of cells removed from each early embryo and, if possible, within 36-72 h, so that embryos identified as unaffected can be transferred without cryopreservation.

Current methods for aneuploidy include sequential FISH for analysis of 9 chromosomes, comparative genomic hybridisation of all chromosomes requiring cryopreservation and multiplex fluorescent PCR. Each reciprocal translocation and each type of Robertsonian translocation require the development of a specific strategy. Current methods for single gene detection include mutation detection and linkage analysis by multiplex fluorescent PCR.

TABLE 4

Advantages of the present invention in prenatal diagnosis and preimplantation genetic diagnosis.

| | Advantages |
|---|---|
| Prenatal diagnosis | Universal screen for aneuploidy (possible exceptions)<br>High resolution detection of unbalanced translocations and common deletions |
| Preimplantation genetic diagnosis | Universal screen for aneuploidy (including translocations) combined with single gene defect linkage detection<br>No requirement for test development<br>Identifies parental origin of aneuploidy |

REFERENCES

Handyside et al (2004) Isothermal whole genome amplification from single and small numbers of cells: a new era for preimplantation genetic diagnosis of inherited disease. Mol Hum Reprod 10, 767-772.

Syvanen, A C (2005) Toward genome wide SNP genotyping. Nature Genetics 37, S5-S10.

Broman, K. W. and Weber, J. L. (2000) Characterisation of human crossover interference. Am J Hum Genet 66, 1911-1926.

Hulten, maternal (1974) Chiasma distribution at diakinesis in the normal human male. Hereditas 76, 55-78.

Hulten M A and Tease C (2003) Genetic maps: direct meiotic analysis. In: Cooper D N (ed) Encyclopaedia of the Human Genome Nature Publishing Group, London Lynn, A, Ashley, T and Hassold, T (2004) Variation in human meiotic recombination. Annu Rev Genomics Hum Genet 5, 317-349.

Tease C and Hulten M A (2004) Inter-sex variation in synaptonemal complex lengths largely determine the different recombination rates in male and female germ cells. Cytogenet Genome Res 107, 208-215.

Meng H, Hager K and Gruen J R (2005) Detection of Turner syndrome using high-throughput quantitative genotyping. J Clin Endocrinol Metab 90, 3419-3422.

International HapMap Consortium (2005) A haplotype map of the human genome. Nature 437, 1299-1320.

Abou-Sleiman P M, Apessos A, Harper J C, Serhal P, Winston R M and Delhanty J D (2002) First application of preimplantation genetic diagnosis to neurofibromatosis type 2 (NF2). Prenatal Diagnosis 22, 519-524.

Stephens M and Donnelly P (2003) A comparison of Bayesian methods for haplotype reconstruction from population genotype data. Am J Hum Genet 73, 1162-1169.

APPENDIX 1

Microsoft Excel VBA macro: SNP analysis (1)

```
Private Sub CommandButton1_Click( )
For i = 1 To X (no. of SNPs analysed)
If Cells(i, 1) = "A" And Cells(i, 2) = "A" And Cells(i, 3) = "A" And Cells(i, 4) = "A" Then Cells(i, 5).Value = 1
If Cells(i, 1) = "B" And Cells(i, 2) = "B" And Cells(i, 3) = "B" And Cells(i, 4) = "B" Then Cells(i, 5).Value = 2
If Cells(i, 1) = "A" And Cells(i, 2) = "A" And Cells(i, 3) = "B" And Cells(i, 4) = "B" Then Cells(i, 5).Value = 3
If Cells(i, 1) = "B" And Cells(i, 2) = "B" And Cells(i, 3) = "A" And Cells(i, 4) = "A" Then Cells(i, 5).Value = 4
If Cells(i, 1) = "A" And Cells(i, 2) = "B" And Cells(i, 3) = "A" And Cells(i, 4) = "A" Then Cells(i, 5).Value = 5
If Cells(i, 1) = "A" And Cells(i, 2) = "B" And Cells(i, 3) = "B" And Cells(i, 4) = "B" Then Cells(i, 5).Value = 6
If Cells(i, 1) = "B" And Cells(i, 2) = "A" And Cells(i, 3) = "A" And Cells(i, 4) = "A" Then Cells(i, 5).Value = 7
If Cells(i, 1) = "B" And Cells(i, 2) = "A" And Cells(i, 3) = "B" And Cells(i, 4) = "B" Then Cells(i, 5).Value = 8
If Cells(i, 1) = "A" And Cells(i, 2) = "A" And Cells(i, 3) = "A" And Cells(i, 4) = "B" Then Cells(i, 5).Value = 9
If Cells(i, 1) = "B" And Cells(i, 2) = "B" And Cells(i, 3) = "A" And Cells(i, 4) = "B" Then Cells(i, 5).Value = 10
If Cells(i, 1) = "A" And Cells(i, 2) = "A" And Cells(i, 3) = "B" And Cells(i, 4) = "A" Then Cells(i, 5).Value = 11
If Cells(i, 1) = "B" And Cells(i, 2) = "B" And Cells(i, 3) = "B" And Cells(i, 4) = "A" Then Cells(i, 5).Value = 12
If Cells(i, 1) = "A" And Cells(i, 2) = "B" And Cells(i, 3) = "A" And Cells(i, 4) = "B" Then Cells(i, 5).Value = 13
If Cells(i, 1) = "B" And Cells(i, 2) = "A" And Cells(i, 3) = "A" And Cells(i, 4) = "B" Then Cells(i, 5).Value = 14
If Cells(i, 1) = "A" And Cells(i, 2) = "B" And Cells(i, 3) = "B" And Cells(i, 4) = "A" Then Cells(i, 5).Value = 15
If Cells(i, 1) = "B" And Cells(i, 2) = "A" And Cells(i, 3) = "B" And Cells(i, 4) = "A" Then Cells(i, 5).Value = 16
Next i
For i = 1 To X
If Cells(i, 5) = 5 And Cells(i, 6) = "AB" Then Cells(i, 9).Interior.Color = RGB(200, 0, 0)
If Cells(i, 5) = 5 And Cells(i, 6) = "BB" Then Cells(i, 9).Interior.Color = RGB(200, 0, 0)
If Cells(i, 5) = 5 And Cells(i, 6) = "AA" Then Cells(i, 8).Interior.Color = RGB(200, 0, 0)
If Cells(i, 5) = 6 And Cells(i, 6) = "AB" Then Cells(i, 8).Interior.Color = RGB(200, 0, 0)
If Cells(i, 5) = 6 And Cells(i, 6) = "AA" Then Cells(i, 8).Interior.Color = RGB(200, 0, 0)
If Cells(i, 5) = 6 And Cells(i, 6) = "BB" Then Cells(i, 9).Interior.Color = RGB(200, 0, 0)
If Cells(i, 5) = 7 And Cells(i, 6) = "AB" Then Cells(i, 8).Interior.Color = RGB(200, 0, 0)
If Cells(i, 5) = 7 And Cells(i, 6) = "BB" Then Cells(i, 8).Interior.Color = RGB(200, 0, 0)
If Cells(i, 5) = 7 And Cells(i, 6) = "AA" Then Cells(i, 9).Interior.Color = RGB(200, 0, 0)
If Cells(i, 5) = 8 And Cells(i, 6) = "AB" Then Cells(i, 9).Interior.Color = RGB(200, 0, 0)
If Cells(i, 5) = 8 And Cells(i, 6) = "AA" Then Cells(i, 9).Interior.Color = RGB(200, 0, 0)
If Cells(i, 5) = 8 And Cells(i, 6) = "BB" Then Cells(i, 8).Interior.Color = RGB(200, 0, 0)
If Cells(i, 5) = 9 And Cells(i, 6) = "AB" Then Cells(i, 11).Interior.Color = RGB(0, 0, 200)
If Cells(i, 5) = 9 And Cells(i, 6) = "BB" Then Cells(i, 11).Interior.Color = RGB(0, 0, 200)
If Cells(i, 5) = 9 And Cells(i, 6) = "AA" Then Cells(i, 10).Interior.Color = RGB(0, 0, 200)
If Cells(i, 5) = 10 And Cells(i, 6) = "AB" Then Cells(i, 10).Interior.Color = RGB(0, 0, 200)
If Cells(i, 5) = 10 And Cells(i, 6) = "AA" Then Cells(i, 10).Interior.Color = RGB(0, 0, 200)
If Cells(i, 5) = 10 And Cells(i, 6) = "BB" Then Cells(i, 11).Interior.Color = RGB(0, 0, 200)
If Cells(i, 5) = 11 And Cells(i, 6) = "AB" Then Cells(i, 10).Interior.Color = RGB(0, 0, 200)
If Cells(i, 5) = 11 And Cells(i, 6) = "BB" Then Cells(i, 10).Interior.Color = RGB(0, 0, 200)
If Cells(i, 5) = 11 And Cells(i, 6) = "AA" Then Cells(i, 11).Interior.Color = RGB(0, 0, 200)
If Cells(i, 5) = 12 And Cells(i, 6) = "AB" Then Cells(i, 11).Interior.Color = RGB(0, 0, 200)
If Cells(i, 5) = 12 And Cells(i, 6) = "AA" Then Cells(i, 11).Interior.Color = RGB(0, 0, 200)
If Cells(i, 5) = 12 And Cells(i, 6) = "BB" Then Cells(i, 10).Interior.Color = RGB(0, 0, 200)
Next i
End Sub
```

The invention claimed is:

1. A method comprising:
   (a) removing one to five cells from a pre-implantation human embryo resulted from in vitro fertilization (IVF);
   (b) isolating genomic DNA from at least one human target cell, wherein the at least one human target cell consists of the one to five cells removed from the pre-implantation human embryo resulted from IVF;
   (c) detecting by oligonucleotide chip or oligonucleotide microarray the genotype of at least 2,500 biallelic single nucleotide polymorphisms (SNPs) in the genomic DNA isolated from the at least one human target cell, wherein detecting by oligonucleotide chip or oligonucleotide microarray the genotype of said at least 2,500 SNPs in the genomic DNA isolated from the at least one human target cell is preceded by whole genome amplification;
   (d) isolating maternal genomic DNA, wherein the maternal genomic DNA is from the mother of the pre-implantation human embryo resulted from IVF;
   (e) detecting by oligonucleotide chip or oligonucleotide microarray the genotype of said at least 2,500 biallelic SNPs in the maternal genomic DNA;
   (f) isolating paternal genomic DNA, wherein the paternal genomic DNA is from the father of the pre-implantation human embryo resulted from IVF;
   (g) detecting by oligonucleotide chip or oligonucleotide microarray the genotype of said at least 2,500 biallelic SNPs in the paternal genomic DNA;
   (h) assessing the statistical likelihood of normal recombination between two SNPs of said at least 2,500 biallelic SNPs in the genomic DNA isolated from the at least one human target cell; and
   (i) in response to a statistical likelihood of normal recombination, implanting without cryopreservation the pre-implantation human embryo resulted from IVF;
   wherein the said at least 2,500 biallelic SNPs are distributed on at least 10 human chromosomes.

2. A method as claimed in claim 1 further comprising:
   isolating genomic DNA from a sibling of the pre-implantation human embryo resulted from IVF, wherein the sibling is affected with an inherited disease;
   detecting by oligonucleotide chip or oligonucleotide microarray the genotype of the said at least 2,500 biallelic SNPs in the genomic DNA isolated from the sibling affected with an inherited disease.

3. The method of claim 1, wherein at least 5,000 SNPs are detected in the at least one human target cell, the maternal genomic DNA, and the paternal genomic DNA.

4. The method of claim 1, wherein at least 10,000 SNPs distributed at an average distance of 0.2 Kb across 22 chromosomes are detected in the at least one human target cell, the maternal genomic DNA, and the paternal genomic DNA.

5. The method of claim 1, wherein said at least 2,500 biallelic SNPs are distributed on at least 15 human chromosomes.

6. The method of claim 1, wherein said at least 2,500 biallelic SNPs are distributed on at least 20 human chromosomes.

7. The method of claim 1, wherein said at least 2,500 biallelic SNPs are distributed on all of the human chromosomes.

8. The method of claim 1, wherein the at least 10 human chromosomes comprise the X, Y, 22, 21, 18, 16 and/or 13 chromosome.

9. The method of claim 1, wherein wherein detecting by oligonucleotide chip or oligonucleotide microarray the genotype of said at least 2,500 SNPs in the maternal genomic DNA and/or the paternal genomic DNA is preceded by whole genome amplification.

10. The method of claim 9, wherein the statistical likelihood of normal recombination comprises detecting aneuploidy.

11. The method of claim 1, wherein the statistical likelihood is assessed based on one or more of the following criteria:
an average number of recombination events for the specific paternal or maternal chromosome, or
distance between apparent recombination events on each chromosome arm and their position relative to each other, the centromere, and the telomere.

12. The method of claim 11, wherein the statistical likelihood (p) of two recombination events between SNP alleles separated by a distance of d centiMorgans (cM) is calculated according to the formula:

$$p=(0.0114d-0.0154)^4.$$

13. The method of claim 1, wherein the two SNPs are adjacent SNPs.

14. The method of claim 1, wherein assessing the statistical likelihood of normal recombination comprises detecting aneuploidy.

15. A method comprising:
(a) removing one to five cells from a pre-implantation human embryo resulted from in vitro fertilization (IVF);
(b) isolating genomic DNA from at least one human target cell, wherein the at least one human target cell consists of the one to five cells removed from the pre-implantation human embryo resulted from IVF;
(c) detecting by oligonucleotide chip or oligonucleotide microarray the genotype of at least 2,500 biallelic single nucleotide polymorphisms (SNPs) in the genomic DNA isolated from the at least one human target cell, each biallelic SNP having allele A or allele B, wherein detecting by oligonucleotide chip or oligonucleotide microarray the genotype of said at least 2,500 SNPs in the genomic DNA isolated from the at least one human target cell is preceded by whole genome amplification;
(d) detecting whether the genotype is AA, AB, BB, or absent for each of said at least 2,500 biallelic SNPs in the genomic DNA isolated from the at least one human target cell;
(e) isolating maternal genomic DNA, wherein the maternal genomic DNA is from the mother of the pre-implantation human embryo resulted from IVF;
(f) detecting by oligonucleotide chip or oligonucleotide microarray the genotype of said at least 2,500 biallelic SNPs in the maternal genomic DNA;
(g) detecting whether the genotype is AA, AB, or BB for each of said at least 2,500 biallelic SNPs in the genomic maternal DNA;
(h) isolating paternal genomic DNA, wherein the paternal genomic DNA is from the father of the pre-implantation human embryo resulted from IVF;
(i) detecting by oligonucleotide chip or oligonucleotide microarray the genotype of said at least 2,500 biallelic SNPs in the paternal genomic DNA;
(j) detecting whether the genotype is AA, AB, or BB for each of said at least 2,500 biallelic SNPs in the paternal genomic DNA;
(k) assessing the statistical likelihood of normal recombination between two SNPs of said at least 2,500 biallelic SNPs in the genomic DNA isolated from the at least one human target cell; and
(l) in response to a statistical likelihood of normal recombination, implanting without cryopreservation the pre-implantation human embryo resulted from IVF;
wherein said at least 2,500 biallelic SNPs are distributed on at least 10 human chromosomes.

16. The method of claim 15, wherein the at least 10 human chromosomes comprise the X, Y, 22, 21, 18, 16 and/or 13 chromosome.

17. The method of claim 15, wherein said at least 2,500 biallelic SNPs are distributed on all of the human chromosomes.

18. The method of claim 15, wherein wherein detecting by oligonucleotide chip or oligonucleotide microarray the genotype of said at least 2,500 biallelic SNPs in the maternal genomic DNA and/or the paternal genomic DNA is preceded by whole genome amplification.

19. The method of claim 15, wherein the statistical likelihood is assessed based on one or more of the following criteria:
an average number of recombination events for the specific paternal or maternal chromosome, or
distance between apparent recombination events on each chromosome arm and their position relative to each other, the centromere, and the telomere.

20. The method of claim 19, wherein the statistical likelihood (p) of two recombination events between SNP alleles separated by a distance of d centiMorgans (cM) is calculated according to the formula:

$$p=(0.0114d-0.0154)^4.$$

21. The method of claim 15, wherein the two SNPs are adjacent SNPs.

* * * * *

UNITED STATES PATENT AND TRADEMARK OFFICE
CERTIFICATE OF CORRECTION

Page 1 of 1

PATENT NO. : 11,214,826 B2
APPLICATION NO. : 12/093912
DATED : January 4, 2022
INVENTOR(S) : Handyside It is certified that error appears in the above-identified patent and that said Letters Patent is hereby corrected as shown below:

On the Title Page

Item (73) under "Assignee", delete "LIMITED" and insert -- LIMITED, (GB) --;

Column 1, item (30) under "Foreign Application Priority Data", delete "0523276" and insert -- 0523276.4 --;

Column 2, item (56) under "Other Publications", Line 32, after "1926." delete "Bruce, S. et al.,";

Column 2, item (56) under "Other Publications", Line 33, before "Global" insert -- Bruce, S. et al., --.

In the Claims

Column 19, Claim 9, Line 21, delete "wherein wherein" and insert -- wherein --.

Column 20, Claim 18, Line 41, delete "wherein wherein" and insert -- wherein --.

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*